US010662486B2

(12) United States Patent
Jia et al.

(10) Patent No.: US 10,662,486 B2
(45) Date of Patent: May 26, 2020

(54) MOLECULAR MARKERS ASSOCIATED WITH SOYBEAN TOLERANCE TO LOW IRON GROWTH CONDITIONS

(71) Applicant: Monsanto Technology LLC, St. Louis, MO (US)

(72) Inventors: Hongwu Jia, Grover, MO (US); Bradley La Vallee, Clarkson Valley, MO (US); Roger L. Lussenden, Grover, MO (US); Jennifer L. Yates, St. Louis, MO (US); Xianghai Ye, Ankeny, IA (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 16/036,361

(22) Filed: Jul. 16, 2018

(65) Prior Publication Data

US 2018/0312932 A1 Nov. 1, 2018

Related U.S. Application Data

(63) Continuation of application No. 14/300,384, filed on Jun. 10, 2014, now Pat. No. 10,059,999.

(60) Provisional application No. 61/833,129, filed on Jun. 10, 2013.

(51) Int. Cl.
*A01H 5/10* (2018.01)
*C12Q 1/6895* (2018.01)
*A01H 1/04* (2006.01)

(52) U.S. Cl.
CPC .............. *C12Q 1/6895* (2013.01); *A01H 1/04* (2013.01); *C12Q 2600/13* (2013.01); *Y10T 436/143333* (2015.01)

(58) Field of Classification Search
None
See application file for complete search history.

(56) References Cited

U.S. PATENT DOCUMENTS

| | | |
|---|---|---|
| 4,582,788 A | 4/1986 | Erlich |
| 4,683,194 A | 7/1987 | Saiki et al. |
| 4,683,202 A | 7/1987 | Mullis |
| 4,971,908 A | 11/1990 | Kishore et al. |
| 5,188,642 A | 2/1993 | Shah et al. |
| 5,210,015 A | 5/1993 | Gelfand et al. |
| 5,217,863 A | 6/1993 | Cotton et al. |
| 5,468,613 A | 11/1995 | Erlich et al. |
| 5,595,890 A | 1/1997 | Newton et al. |
| 5,616,464 A | 4/1997 | Albagli et al. |
| 5,762,876 A | 6/1998 | Lincoln et al. |
| 5,776,760 A | 7/1998 | Barry et al. |
| 5,800,944 A | 9/1998 | Blonsky et al. |
| 5,876,930 A | 3/1999 | Livak et al. |
| 5,945,283 A | 8/1999 | Kwok et al. |
| 6,004,744 A | 12/1999 | Goelet et al. |
| 6,013,431 A | 1/2000 | Söderlund et al. |
| 6,030,787 A | 2/2000 | Livak et al. |
| 6,090,558 A | 7/2000 | Butler et al. |
| 6,207,367 B1 | 3/2001 | Helentjaris et al. |
| 6,225,114 B1 | 5/2001 | Eichholtz et al. |
| 6,399,855 B1 | 6/2002 | Beavis |
| 6,503,710 B2 | 1/2003 | Gut et al. |
| 6,613,509 B1 | 9/2003 | Chen |
| 6,799,122 B2 | 9/2004 | Benson |
| 6,803,501 B2 | 10/2004 | Baerson et al. |
| 6,913,879 B1 | 7/2005 | Schena |
| RE38,825 E | 10/2005 | Barry et al. |
| 6,959,617 B2 | 11/2005 | Deppermann |
| 6,996,476 B2 | 2/2006 | Najarian |
| RE39,247 E | 8/2006 | Barry et al. |
| 7,134,351 B2 | 11/2006 | Deppermann |
| 7,238,476 B2 | 7/2007 | McKeown et al. |
| 7,250,252 B2 | 7/2007 | Katz et al. |
| 7,270,981 B2 | 9/2007 | Armes et al. |
| 7,282,355 B2 | 10/2007 | Shi |
| 7,297,485 B2 | 11/2007 | Bornarth et al. |
| 7,312,039 B2 | 12/2007 | Barany et al. |
| 7,454,989 B2 | 11/2008 | Deppermann |
| 7,502,113 B2 | 3/2009 | Deppermann et al. |
| 7,582,806 B2 | 9/2009 | Sebastian et al. |
| 7,591,101 B2 | 9/2009 | Deppermann |

(Continued)

FOREIGN PATENT DOCUMENTS

| | | |
|---|---|---|
| EP | 0 050 424 A1 | 4/1982 |
| EP | 0 084 796 A2 | 8/1983 |

(Continued)

OTHER PUBLICATIONS

Funke et al., 1993, Physical mapping of a region in the soybean (*Glycine max*) genome containing duplicated sequences, Plant Molecular Biology 22: 437-446.*

Borevitz et al. "Large-Scale Identification of Single-Feature Polymorphisms in Complex Genomes," *Genome Res.*, 13:513-523 (2003).

Charlson et al. "Associating SSR Markers with Soybean Resistance to Iron Chlorosis," *Journal of Plant Nutrition*, 26(10-11):2267-2276 (2003).

Choi et al. "A Soybean Transcript Map: Gene Distribution, Haplotype and Single-Nucleotide Polymorphism Analysis," *Genetics*, 176(1):685-696 (2007).

Cox et al. "Relationship Between Coefficient of Parentage and Genetic Similarity Indices in the Soybean," *Crop Science*, 25:529-532 (1985).

(Continued)

*Primary Examiner* — Bratislav Stankovic
(74) *Attorney, Agent, or Firm* — Arnold & Porter Kaye Scholer; Lawrence M. Lavin, Jr.

(57) ABSTRACT

The present invention provides methods and compositions for identifying soybean plants that are tolerant or have improved tolerance, or those that are susceptible to, iron deficient growth conditions. The methods use molecular markers to identify, select, and/or introgress genetic loci modulating phenotypic expression of an iron deficiency tolerance trait in soybean plant breeding. Methods are provided for screening germplasm entries for the performance and expression of this trait.

19 Claims, No Drawings

Specification includes a Sequence Listing.

(56) References Cited

U.S. PATENT DOCUMENTS

| | | | |
|---|---|---|---|
| 7,611,842 | B2 | 11/2009 | Deppermann et al. |
| 7,666,644 | B2 | 2/2010 | Castle et al. |
| 7,685,768 | B2 | 3/2010 | Deppermann |
| 7,977,533 | B2 | 7/2011 | Sebastian et al. |
| 2005/0015827 | A1 | 1/2005 | Podlich et al. |
| 2005/0204780 | A1 | 9/2005 | Moridaira et al. |
| 2005/0216545 | A1 | 9/2005 | Aldrich et al. |
| 2005/0218305 | A1 | 10/2005 | Tsukamoto et al. |
| 2006/0042527 | A1 | 3/2006 | Deppermann |
| 2006/0046244 | A1 | 3/2006 | Deppermann |
| 2006/0046264 | A1 | 3/2006 | Deppermann et al. |
| 2006/0048247 | A1 | 3/2006 | Deppermann |
| 2006/0048248 | A1 | 3/2006 | Deppermann |
| 2007/0204366 | A1 | 8/2007 | Deppermann et al. |
| 2007/0207485 | A1 | 9/2007 | Deppermann et al. |
| 2008/0256660 | A1* | 10/2008 | Jenkinson ............ C12Q 1/6895 800/267 |
| 2009/0025288 | A1 | 1/2009 | Deppermann et al. |
| 2009/0036308 | A1 | 2/2009 | Guida, Jr. et al. |
| 2009/0215060 | A1 | 8/2009 | Deppermann et al. |
| 2010/0086963 | A1 | 4/2010 | Deppermann et al. |
| 2010/0099859 | A1 | 4/2010 | Malven et al. |

FOREIGN PATENT DOCUMENTS

| | | |
|---|---|---|
| EP | 0 201 184 A2 | 12/1986 |
| EP | 0 237 362 A1 | 9/1987 |
| EP | 0 258 017 A2 | 3/1988 |

OTHER PUBLICATIONS

Cui et al. "Detecting single-feature polymorphisms using oligonucleotide arrays and robustified projection pursuit," *Bioinformatics*, 21:3852-3858 (2005).

Dahiya et al. "Effect of Salinity, Alkalinity and Iron Sources on Availability of Iron," *Plant and Soil*, 51:13-18 (1979).

Diers et al. "Possible Identification of Quantitative Trait Loci Affecting Iron Efficiency in Soybean," *Journal of Plant Nutrition*, 15(10):2127-2136 (1992).

Funke et al. "Physical Mapping of a Region in the Soybean (*Glycine max*) genome containing duplicated sequences" *Plant Molecular Biology* 22: 437-446 (1993).

Gonzalez-Vallejo et al. "Iron Deficiency Decreases the Fe(III)-Chelate Reducing Activity of Leaf Protoplasts," *Plant Physiol.*, 122(2):337-344 (2000).

Goos et al. "A Comparison of Three Methods for Reducing Iron-Deficiency Chlorosis in Soybean," *Agronomy Journal*, 92:1135-1139 (2000).

Goos et al. "Seed Treatment, Seeding Rate, and Cultivar Effects on Iron Deficiency Chlorosis of Soybean," *Journal of Plant Nutrition*, 24(8):1255-1268 (2001).

Hartl et al. "Genetics Principles and Analysis," *Jones and Bartlett publishers*, 4:128 (1998).

Hintz et al. "Population Development for the Selection of High-Yielding Soybean Cultivars with Resistance to Iron Deficiency Chlorosis," *Crop Science*, 27:707-710 (1987).

Karkosh et al. "Seed Treatment for Control of Iron-Deficiency Chlorosis of Soybean," *Crop Science*, 28:369-370 (1988).

Lin et al. "Molecular Characterization of Iron Deficiency Chlorosis in Soybean," *Journal of Plant Nutrition*, 23:1929-1939 (2000).

Mullis et al. "Specific Enzymatic Amplification of DNA In Vitro: The Polymerase Chain Reaction," *Cold Spring Harbor Symp. Quant. Biol.*, 51:263-273 (1986).

O'Rourke, Ph.D., "A Genomic Study of Soybean Iron Deficiency Chlorosis" Thesis, University of Iowa, pp. 1-191 (2008).

O'Rourke et al. "Integrating Microarray Analysis and the Soybean Genome to Understand the Soybeans Iron Deficiency Response" *BMC Genomics* 10:376, with Additional files. 4 and 6 (2009).

Padgette et al. "Development, Identification, and Characterization of a Glyphosate-Tolerant Soybean Line," *Crop Sci.* 35:1451-1461 (1995).

Service, "The Race for the $1000 Genome," *Science*, 311:1544-1546 (2006).

Wang et al. Association Mapping of Iron Deficiency Chlorosis Loci in Soybean (*Glycine max* L. Merr.) Advanced Breeding Lines *Theor. Appl. Genet.* 116: 777-787 (2008).

* cited by examiner

```
                         SEQUENCE LISTING

<160> NUMBER OF SEQ ID NOS: 147

<210> SEQ ID NO 1
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 1
ttgctttcat ttgttacaaa gcaacaattc tctctttagt acatgttgag caaagtgaat    60
caggcaactt atcaaagtag tcccatgttg catgataaag aagaggaaaa tagaaagaat   120
tttcagttaa ccgaaaaagt acaatgtncc ntttagataa attgaaaatg aaacaatatg   180
ttatcatgnt tctatcctcc aattcataca tgacctttt gctttacgtg aaggaggacc    240
tcatccaatt gttggataat caaaatgaga aaagtcctca tctnaatgat tatttctctc   300
g                                                                    301

<210> SEQ ID NO 2
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 2
ttaacctnct atatgtatct cagtctcttc cttttcttc atttgctcat aattagaact     60 ataaatagg cttaacccga caaactgacc cattagcctg ttagggcggg tcaagctggg    120
cccaagaaaa ttcggcctga atagaacttg gtcaatctgg gtactctgat aggcccagac   180
cgagctcaag aattacaaat ccaagttcaa tcaggnctat tatagtccaa cattattttt   240
attttttatc ctttaaattt atataaatcc agacaaaatt ttaaaacggg ccattgggct   300
a                                                                    301

<210> SEQ ID NO 3
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations
```

<400> SEQUENCE: 3

```
gtatacagaa acagacaata atctcttact taattttcca ctagtcattg tttaacccaa      60
tgctggaaag tgatctttct aaagactcat tttatcatat tgaaaagtag ctttgaccga     120
ataaagcatt gtacattctt ttttgtgctt tgcggtaggt tccattggaa tgcacttcga     180
tatgtttaca tctaaatcca attttgggtc atacattcat tattatgttt ctaagccata     240
aatataagat aagtgttgca tatatttaag tttattggat tgcacttcgt attatntata     300
t                                                                     301
```

<210> SEQ ID NO 4
<211> LENGTH: 378
<212> TYPE: DNA
<213> ORGANISM: Glycine max

<400> SEQUENCE: 4

```
agatctaaca aggtaatttt tcccttaact atttgaaact cattatcaca acttggtaaa      60
agttaccttt caattgtcaa atttaaaacc catcacataa aatgccacaa atacatgcca     120
caccaaaatt tgcaagagaa ttcaaccaca ctgcagatct gcttcaggta gcagttcatc     180
gtgatacttt caccatactc aagcagaaag gtatatacaa agtactcatt ttttttgtt      240
aagaatgtga gggtaaagac caatttctga cccaatctgt aagagttgcc acatttctac     300
taacgtcttc tatattatca ctcttcattg caatcacttt ctcctccgag taactttctt     360
tagcctcctc aagcaaaa                                                   378
```

<210> SEQ ID NO 5
<211> LENGTH: 760
<212> TYPE: DNA
<213> ORGANISM: Glycine max

<400> SEQUENCE: 5

```
gccttgggtt cttgatgttg ccaagaaatt tgggctactt ggtgctactt tcttcactca      60
gacatgcaca acaaacaaca tatacttcca tgtttataag aagttgatag agttgcctct     120
tacacaggca gaatatttgt tgccagggtt gccaaaactt gcagctgggg acttgccatc     180
tttcttgaac aaatatgggt cctatccagg ctactttgat gtagttgtga atcaatttgt     240
caacattgat aaagcagatt gggttcttgc aaacagtttt tatgaactgg agcaaggggt     300
aagtgacttg actagctgaa aattctcttc attaatttga tttgtactta tttgttggaa     360
tgaattagac agcagtagtt atctgggtaa aaagttttc cttcaaattt tggtcaaaat     420
ttgtcctagt tcctattact tcaggatgat tctggtcttc tttttattt ataattgatg      480
gattttgtct ctcatcctag tatcctaagt tccataaaaa gagaaaaaat tcatcaatta     540
taaaaagaat tcaaagacca aaatatcat ttttaaagta taacgactaa gaacaatttt      600
gattgaaatt agagagatct agaatacatt tttatcctag ttattttgtt ggataatatt     660
gatgattgaa atttgaaatg aaatttattg taggttgtgg attggctggt gaagatttgg     720
ccattaaagc caataggacc atgcctgcca tctatctact                           760
```

<210> SEQ ID NO 6
<211> LENGTH: 301
<212> TYPE: DNA
<213> ORGANISM: Glycine max

<400> SEQUENCE: 6

```
taggacccat atttgttcaa gaaagatggc aagtccccag ctgcaagttt tggcaaccct    60
ggcaacaaat attctgcctg tgtaagaggc aactctatca acttcttata aacatggaag   120
tatatgttgt ttgttgtgca tgtctgagtg aagaaagtag caccaagtag cccaaatttc   180
ttggcaacat caagaaccca aggcatgaaa gcatcataga taacacaatc tggagggtgg   240
cttgaccctg caagcttctg aacaagctca gcaaagtttt gtgatccaac cctccaaaag   300
g                                                                   301
```

<210> SEQ ID NO 7
<211> LENGTH: 301
<212> TYPE: DNA
<213> ORGANISM: Glycine max

<400> SEQUENCE: 7

```
agaacagaac aattcattta tgcggttatt gtttggtttt gcaggttaga gctgcagagc    60
tgaggaagat attggtggag ctgggccgg tatgtaatgc tggattgaat gcataataat    120
tcagttttag tagtggtttt cttaattgc tatttttcttt taattggttg atttggttca   180
ttgctgtttt atactacttt tttgcaggca tatatcaaaa ttgcccaggc tatatcatcc   240
cgtgctgtaa gttttggttt atctgtcaca ttattaaaac tgatctccat gttctttggt   300
t                                                                   301
```

<210> SEQ ID NO 8
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 8

```
tatcctttgc gatggtttgg gcatgaatac ttgatactta cctagagaaa aggttaaatt    60
taatatcatc atgatcttct tcctaaatga tgttgtgtgc cttttgagtt tcgagattta   120
gttcttggat atatgcctga agtgtttctc ccttgaaaac aagttaaggc atataggaa    180 aatttgtctt tacacattct tgtttgttgc ttgctgaaaa aagttgagaa ttctgctgat   240
gcactatggt atggctattg tagggggnaa agttgtctga agtgaaggat ctctacctga   300
t                                                                   301
```

<210> SEQ ID NO 9
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 9

```
ttttcttgtt ggntcgtaaa ttgcaatatg gggatctttt ttggatttta cttgttttat    60
tatacctgac ttttagtcaa tcgttcagca ataggtatat taaacttgga acgctanatg   120
gacaatcatt ttactgtttt gtttatccta ataaaaaaaa ttgtacttt catcaatgac   180 atgtaggaaa gcanacaggc cagtcctgac aagaatcaaa tactgtacat ggaggagttg   240
tcgttagttt taaatcaagt tgaatccatt caagacattc ttcctataat ttctgtcatt   300
c                                                                   301
```

<210> SEQ ID NO 10
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 10

```
aatgaaccaa tttgaaggaa acaaacaaat taaagctgta aaaatnaana atatccaatt    60
attacccccgt gttcttttag aaattgaatg gaatcatgtg tactgcacta taaatgacca   120
ccaaataaat ggtttattta acaaagtgga atccatgtct tcaaacaagt agcacgaagg   180
acatcaaaac catagttcac tgaaggacgc tagtttaaat ttcatcnttt tagtgaactt   240
caatgtaatt aaataaatca aggatgggaa tatacatgtt gtttgaagac tcattggacg   300
g                                                                   301
```

<210> SEQ ID NO 11
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 11

```
tttcttggtt gaaatttccg caacctcctc ctttgtaatt tccttgacct ttacctctat    60
aatttcctct tcctccattg ttgagattat nacaaacttt gctttgtgca ctttgacttg   120
attcaacaac acttttgaga ttcacctgac tcttaaggc ttcttcagtt acttttttcaa   180
tcttcttcaa gattctactc atgtgacttt tgatgcttc cctgcaaata tgctattgtc   240
gtggtgtaga atgggatggt gttaggattt tgtccactac cttgttgtct aggatgtctt   300
c                                                                   301
```

<210> SEQ ID NO 12
<211> LENGTH: 301
<212> TYPE: DNA
<213> ORGANISM: Glycine max

<400> SEQUENCE: 12

```
gtttactaac tactatatgt tttgttgtgt tttgtataac ttcattcaat tgtacaggaa    60
tgaaaatgaa tacgatttta ttgggaagat tgttaaagag gtctcccaaa aaattaatcg   120
cactcttta catgttgtgg attacccgt tggattggag tctcgagtgc tacaggtaat   180
ctcacttta gatgatggtt cagacgaagt ccacatggta ggaatccatg gaattggtgg   240
ggtaggaaaa acaacaattg ctcgagcagt ttataatttg attgctgatc aatttgaagg   300
g                                                                   301
```

<210> SEQ ID NO 13
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 13

```
ataaaatatt attttattttt attaaaaaga aaagaaaaaa ataattttca ataacaacaa      60
cttaattatt tttatattct taatttactt gtgaatgaag cttctgatga tgcaacatat     120
gtgatgagta aagaaaagag gatttcaana actcgttgat gtggaatacc gagagtatct     180
cattgattcg ttagaatacc aagaggttga tataagggtt tgactgctcg ttgattcaag     240
agaaagccga gggttgagaa ttgagaaaaa cttnaaattt tgttcaata ataatctttt      300
c                                                                     301
```

<210> SEQ ID NO 14
<211> LENGTH: 301
<212> TYPE: DNA
<213> ORGANISM: Glycine max

<400> SEQUENCE: 14

```
tgacattact aatgtgcaca ttttttgtggt taaattgtgc tttggacctg aagggaact      60
gataaaatag aattcataaa gcttgaaggg tacaacaaca tacaagtgca atggaatgga    120
aaagccttcc agaagatgaa gaacctgaga attttgataa ttgaaaatac aaccttttct    180
acaggccctg agcatctacc aaatagtttg agatttctag actggagctg ctatccttca    240
ccatctttac catctgattt caatccaaaa cgagttgaga tactcaaaat gcctgaaagt    300
t                                                                    301
```

<210> SEQ ID NO 15
<211> LENGTH: 409
<212> TYPE: DNA
<213> ORGANISM: Glycine max

<400> SEQUENCE: 15

```
ccaagatggg aaagagttga gtttagaagt gtttccaaag gccattcttg tttgccatct      60
tgatcccagg cattatcatc atcttgacct gtattatctg tacatgagtc ctaataatgt    120
catccaagta tgcagtccta atctgtatat gctctgtgat ttcgatttgt tgttccaaaa    180
gcttgcattg ggtgtcgaga aggactggtt tcgcagatgc aggaaatggt caatgaattt    240
ctcgtttcga aaaagtttc ctaagattgc ggtatgttgt tctataatat ctagattgaa     300
aagtgtcatg gaaatggtgt tgattttgaa gttcagcgta ctcatcaatg gcactatgca    360
atttagttct tcatgtaatt acatatttag aacatgggac ccgataatc                 409
```

<210> SEQ ID NO 16
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 16

```
agacaattaa taagcatggc ctcntccaac tccaagaaat gctaccctct gaaatactca      60
aggagaaata tatcaaagtg ggagatgttt actgagtaat tccaataata aaaggaggc     120
ttgaacaaaa gaaggttctt ctggttctag atgatgttga caaattagag cagttaaaag    180
tacttgcggg acaatatgat tggttaggct ctggaaggac aatcattgtc accacaagag    240
agacaaacac ttgctagcta ctcatggagt gataaactta tacgaggtta aaccattaaa    300
t                                                                    301
```

<210> SEQ ID NO 17
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 17

```
attatatcta taataattta tgattatacg taagagattt tgttacatta ttcgtacata      60
attattaata aaatgattta nttanatcga tagaaaagtt agaaatccac caaaaatcat     120
tttaacattt ttttcaaatc tattgattat ttttaacaac atattagnaa ttcgtttaat    180
ttaacaatat attagtaatt tgtctaatta gggcataact ggttggattt ttttatttaa     240
aatccaagca tatactcatt ttggcccatt ggttacgcaa aaactctaca tatgccgtaa    300
c                                                                    301
```

<210> SEQ ID NO 18
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 18

```
tattgttagc acattgccct ctatcagttc atncctcaaa tctgagcaaa ctaagctttg      60
atgtctctca cataaaccga ttcaacacaa caatgtcatt ttcattgtca agaaggttca    120
gctcttttct ttcaaacctc acttcccctc cttgctttca cttagcctcc ccattgacaa    180
tgacaatgtt gttgatgatg tgttccccaa ttcaatgaca tgctccttgt gcgtcatacc    240
ccacccacca tctaattttaa caagatgtta ggatcattnt aaagatgaag cattatccca     300
c                                                                    301
```

<210> SEQ ID NO 19
<211> LENGTH: 301
<212> TYPE: DNA
<213> ORGANISM: Glycine max

<400> SEQUENCE: 19

```
gcagtcagat ccagcatagc atgaattgca ttcacaacga gacttattca tatctttaag      60
aataagacca tctaagtagg ctcttccatg tcctgaacat ggtattgctg ccacagcctc    120
agcttcttct gcagctcttg tgctccaagt tggctcccat tctcccatac atacaaacgt    180
gctaattgag gcacacaata taataataaa ttttaatttc attggactttt ggacttgttc    240
ttttggcgat tctagtcttc gtttctttgt gaaatcttca agcaatttct tggttgcact    300
t                                                                    301
```

<210> SEQ ID NO 20
<211> LENGTH: 1154
<212> TYPE: DNA
<213> ORGANISM: Glycine max
<220> FEATURE:
<221> NAME/KEY: unsure
<222> LOCATION: (1)..(1154)
<223> OTHER INFORMATION: unsure at all n locations

<400> SEQUENCE: 20

```
tgattcgcca gcttgctgcc tgcgggcaca tttctccata tcagaccaca cctctctttt      60
ctgtaagcct cttattggtt ccctaacgaa tgttgttaat tacattgttg ttctgactat     120
ttattcagct tcggttgtag ccacggattc atgacagaga ttatcaactc atgcttagtt     180
cgaagactat tttaactgtt ttagttttga gttcagaata aagcacgcag cagaggtatc     240
tatctcctca gcttaaagct tttcaattca tcactttgaa tattattttt gttttttag      300
tgagctataa cacaatcaga cttgaaaaat agtatcttat agaaaagtca attacaaatt     360
ttcttgtgaa atataaccac taaatcacat gaaaaaaata tgnaataatc gagaattaaa     420
aagttgagtt ttaggattta aggttttatc tcctttaga  aataccagag ccatacaatt     480
ggtgtgcagt cttctccaat cttctatctt tattacattt ttattttgtt tttctaattc     540
tttttttaac tatttaatta gttagnttta ttttgttttt catttttta  attagttaca    600
tgacatatca caaataactt taaaattgct gactgatatg atcgaccaca tgatcacatt     660
taactgcaca agcaaattga gttaggaaaa naattataat ctgatatttc taaaatttta    720
gaaattaaat gcaaagaata aaattcaaag gactacatat aaatttggtg tattttcaga    780
ataaaaaaac atatttaatc cctctatata ataatgaggt aggaacgggg aagaattttc    840
aaatattaat gtgaatacaa ttttctccta tagttcatta tatttcgacc gtcttaattt    900
gtccttactc ttgaaaactt attaagctga aattttacc  tatatctaaa tgcatggaca    960
acatggctac ttcacttcag aaatctcgaa gtgcaaccaa gaaattgctt gaagatttca   1020
caaagaaacg aagactagaa tcgccaaaag aacaagtcca aagtccaatg aaattaaaat   1080
ttattattgt attgtgtgcc tcaattagca cgtttgtatg tatgggagaa tgggagccaa   1140
cttggagcac aaga                                                     1154
```

<210> SEQ ID NO 21
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 21

```
cctttaaaac gttacaccat atccattggt ggaagaggag ggatggaaaa gnaagggtcg      60
ttgcttaagg acttnttctt aggttaatga cattaatatg tgaaaattta aaatacattc     120
ttttaattg  acgttacata acatgattgg agggggcatga aaagggacag acttttagga   180
ggaatgtgat ttcaatccgt ttgaaataat aagaaatata ttagaacggg ttgaatatta    240
gataatttat tataaatatt tattttaata aaataagtat tttttttacta aattattttt   300
a                                                                     301
```

<210> SEQ ID NO 22
<211> LENGTH: 910
<212> TYPE: DNA
<213> ORGANISM: Glycine max

<400> SEQUENCE: 22

```
actaaaacta cctcaactgt tatagatgtg gtcatttcac ttaaatactg ctttagcaaa      60
tgtccatagc aattgttcag tgtcaatgct gctactgcac cagctattgt gttccatttc     120
ttcaaaattg gactataatt ttgtctctct ttcaatgcca aatattcagt ttcctgagct     180
```

```
aattgaagca taacttcacc tatttctttc tttgtttcag actcagcaga tttggcattt    240
gctgcttcca tcatctacag tcattaggca acaaagacat tatgatattt tcttttact    300 tttaaattaa aaagcagaaa atactataag tttgacacca ttagggatta aaaagcagaa    360
aatactacaa gcagaaaact ctacaagtta tatacatgct tctaacgtat caaccttttg    420
gattgtttct taacaaatac ctacctttc aaaagcattt ttcaaggaag aacagatata    480
gtcatcaatc cggccctcag aggaattcgc tctagttttt tctcctttt cttgcctttc    540 ttcagaattt gtaacatctc ccaaaatctt ggatgctaat aacaccacag gggagaaggt    600
tttcaatttg tccaatatca ccctccctcg aaatacctct gggagttaaa gaaaccttt    660 atctgccccc ttcttggcgg gaactgagga cacatttcaa tatcttcaaa ataaccagga    720
ctccccttct ctttcttaaa ctcatttgcg ccctccattt ataatgtttg gaaggcaaaa    780
aagggaggtt taatttccca tttctcattt gtggaacatc ccctgaaaac acttgtgtgg    840
gcttttccca cggggccttt ttttaaaaga atgtcctttt taaaaaagta tcactctcaa    900
acatgcggga                                                           910

<210> SEQ ID NO 23
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 23
tcccttagct gaaanaaaag gtcaatgtca gtatagggac atggaagtct ttcattgant     60
attactaatg gagttatggt gtttattttt gtatgtccaa tttccatagg gcatagtgcc    120
actcaattct ntaattgata tagatttctt ctgagttctc tttgtaaatt tccagccact    180
tgtatgtgca gtggtctttc attttttttgg tttgctataa tcaataggat taatacnaaa    240
gtgctgtttg gttagtggtt ttcaaattta cagttcagta taaagttatc caggtaatac    300
a                                                                    301

<210> SEQ ID NO 24
<211> LENGTH: 301
<212> TYPE: DNA
<213> ORGANISM: Glycine max

<400> SEQUENCE: 24
attggtcaaa ataaaacgtc cacgtgcact tgaatgatga gtttgaaccc ttattttgtg     60
tgtgtgaatg atgatgagta tgaagctatt atgtaaaaga tgatgtgaac aaagattcca    120
ataatttaaa aacaggcaag tggcatatat tattagactg gagatcactc aagtcaaatt    180
taatgttatt agttattact agctagaggg atagttacgg actttgcatg gtgagggaac    240
tcaatttaaa tgtaacaaga attttttattt tttttaagta acaagaaaaa attgaataaa    300
a                                                                    301

<210> SEQ ID NO 25
<211> LENGTH: 864
<212> TYPE: DNA
<213> ORGANISM: Glycine max
<220> FEATURE:
<221> NAME/KEY: unsure
<222> LOCATION: (1)..(864)
```

<223> OTHER INFORMATION: unsure at all n locations

<400> SEQUENCE: 25

```
ttgttttctt ctctgtattt acaatagggg aaagatgcat gaagcaatac gtcttgtgtt      60
gtcttagtga gatgctttgt ctcatggaca aaggagttat aaagctttat aatctgacag     120
tttttctttt tttcttaccg aactgtctgt ctgctcaaga tggtgcatgc ttagttttgg     180
tttatggaat tcaggaagat aaggaagtat cttgaatttg agcttttaat caatttctat     240
atgcntattg tgatggtagt tttcatttaa aacaaaaatt gtgtttgtca gttggggtta     300
caatcactgg atcgcatcat ttttatgttg gatggcattc gtgtcaatat attttatctg     360
gttctgtgct aagctaccat ggaggagttt atgtcttgtt ttggtgaaat ttcttctctt     420
tgattaaaag tgaagttaaa ctggaaaaaa atgagattta attaatgaac gagtgacaaa     480
tggtatgggt ttggtttttg gtttgtttat attggtttaa catgggatgt tgcgatgata     540
tagagggggtc catgctatgt tctgtatgat accaataagc ttgtggtaga gtaaactcca     600
aaaggatgaa gaaaaaagtt agcataaggc atagagtgca ttattatgtt aaagaatgag     660
aaattgcaat ggcttagagt gcattattat taactatatg ctggaatata tatgataagg     720
ctccattggt ttatgagaaa ctacgggtgg agatttttccc ccctattaaa tagtaacaaa     780
tttggaagat taaatacaca aatgttcact tctcttgtgt atgttggtct ctcagtgctt     840
gcatatggta gtaatctgca ttat                                             864
```

<210> SEQ ID NO 26
<211> LENGTH: 1068
<212> TYPE: DNA
<213> ORGANISM: Glycine max
<220> FEATURE:
<221> NAME/KEY: unsure
<222> LOCATION: (1)..(1068)
<223> OTHER INFORMATION: unsure at all n locations

<400> SEQUENCE: 26

```
cccaggcatt aaccagggag atggcacaaa gttgaacaat cacattaaaa ttattatttt      60
aaccagctcc accaatgaac catactatca aggctctatc agtttgcttc caaagtcggg     120
cttccttaca caaacagaca agacaatgct tacataagac agacaaaact gctcatttac     180
actgttttgga agggatgaat atgggaggga agaaacacag ataacaatgt catttccttt     240
gtttggttgg agaggaagtg gaaagaaaat gagaagaaaa gttgacttct agagataaaa     300
attcaaactt ttttgtactt tctctccaat tcaatttca aacttttctc tcctccctca     360
cttttctttcc tctcgaccaa acatagggct aaagttgcac aattcaaaaa attacactct     420
cccaaagcaa ctttgacaaa ctcaaccaat agctttgacc taactaagag acacnagctt     480
gttcacacat ctctccccca ctagaaaaga caaaactcta cagaaaaagc caaaaaccag     540
ctgcagctta atttcattta gcattgtgct tttggatcca ctataggcta ctcggatcca     600
atggttgttt caatggaatt gtgacttccc tctcttcttt gtaataaata aatctttttt     660
tgtcatcaaa tatatgtaaa acttatcctt gttaaatata accacaactt cctaataata     720
tactaccaat tttttttaat caataacaag aaaaaatgt ctaaccatta gtcatttgct     780
atgcaagtga aaacatcctt tggaacccat gttatccgaa gtgacacgat gatttgagtc     840
tcatatgtga gaatcaatat ttaacattta attttagtag ataaataaac cccaaaagat     900
aggaggtaga aaccatgctc agatgtgtat aaagaaggtt gtacctttttg ggactttttc     960
ttttttcccct catcagcttc ttcactctct tcactttcaa catatgatac cttcctgact    1020
```

```
gtcctactag aagtgcgaat ctcactgttg cgcgaagaaa aacctgtg          1068
```

```
<210> SEQ ID NO 27
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 27
tgttaaaagt ttaaacgtcg tataatctga aatggataaa gtgtttttt tnnaaaaaaa    60 tatttaaata ttaaaaattt ctctagagaa acaatcttat attataattg ttatcaaatg   120
gttctataga ttatatatat aagcaaaatc tttatgttag tgattctaag gactttaaaa   180
cttcaataat cctcggaagg ttataatatt ttaattctng aattacattt tgaatcaaat   240
agttcaacag ttttgtttct taacttaaaa tcaaattgat gtttcacacc aatgagtctt   300
g                                                                  301

<210> SEQ ID NO 28
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 28
ctttgtcacc atgttngttt cacagtcacc tacngttatt tattacacaa attcttnacc    60
atgcattacc tttttaagtt naggcaaata tttttatatt tttntttacc aaatcaaact   120
ttatgcaaat taggaataaa ataagttag attactcaac gggaggcttg gccaatatga   180
cttaacctac atcaggccta tgggtcaaat tggactttt cngaaaataa attattccaa   240
gactttcatt aaaaaanaaa aaacaaaaaa cacatatatt tcaaacttaa aagaaaaaa   300 g                                                                  301

<210> SEQ ID NO 29
<211> LENGTH: 301
<212> TYPE: DNA
<213> ORGANISM: Glycine max

<400> SEQUENCE: 29
aatttaggaa aaagacacgt atattctcta gttttttatt ttattttgaa gactttcata    60 attcttttg ttttagatta ggatgattaa tcaaagtaaa caccgcccct agctttcttt   120
ttaacttgca ttacggataa cttaaccccc ttgctttgca cccaattaaa aagcaataca   180
ttcacgtgga gatacgagag tgactacata tgatttgtgg gagagaaaaa ggaataagaa   240
ggaaaaagta aatgaatgac atggataagt acatatatgg gtcctcactc atattagtca   300
c                                                                  301

<210> SEQ ID NO 30
<211> LENGTH: 301
<212> TYPE: DNA
<213> ORGANISM: Glycine max
<220> FEATURE:
<221> NAME/KEY: unsure
<222> LOCATION: (1)..(301)
```

<223> OTHER INFORMATION: unsure at all n locations

<400> SEQUENCE: 30

```
ggaaccaaaa ctaccagatg taacaactcg tgttgaatca tcgatggctc ccatgtacct    60
cagcatacca tattcaagtt ctgcaaatcc ctgcacttca atcctcttag ttgaaggaac   120
attcaagttc aaagtctgtt aatagattaa aaattcactc atctgctaaa ttaactattt   180
tgnacattac tattggtata aaatgtcaac ctaacacatg agtcacctac taactagtga   240
ggtctcggga gggtagatat actcagctcc accctcataa gctgagaggc tgtctctagc   300
a                                                                   301
```

<210> SEQ ID NO 31
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 31

```
aacttgagtg tntnttttt tcctttcaaa tattcttccg ttctagtccc tgacctaagt    60
ctattttctt gctgtaaagg ttttttcggt cgattggagt ccagatggag agaaggtagc   120
ctctggtggt aaggataaag tgttgaagtt gtggatgggc taggctaatt tttggatgan   180
tattgggaat ccaacgaagt acaatctcaa tggagttttg cggatgcatg gatttcatgg   240
aaatcaatgg ttggtattat gtggatgcaa ggtctttaaa ttatatagac agcatagaag   300
a                                                                   301
```

<210> SEQ ID NO 32
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 32

```
caaaatgaaa tatttatttt tactctnttt ccttttaat tacactcttt cagtaaaaan    60
aaaanatgcc atgttttaaa ccttgtatcc ttattttaat tttattat aaaatacncc    120
agatataaaa caggacgtac attctgtcat nttttaacac cttcgggcat atatgagaag   180
aggattctgt gttttgactt acacaagtac aacaaaggcc atgttgttca gtgacagtac   240
tgccttattc agttatttac cttttcaaaa taaaaaagtt atttacttgg agagtttcca   300
a                                                                   301
```

<210> SEQ ID NO 33
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 33

```
gccgggttaa gattatcctt atatccaggc cttttattt gctnatgaat aaaacactaa    60
tcgttacaat aattgaggtg gacaatatga gatgaatgaa ttttcaatta cttcattcaa   120
```

```
cctaagaaat antgatgctt cttttcntga gtctcctcat gttctttctt ctcatgatgc      180
tcaggatctt tatgggcctt ctgcctctca tgctgtaggc atagatgatt aaacaaaatt      240
tgccatgtta tttaatattt gttactttaa aaaatnataa caattcacca aacttaaatg      300
a                                                                      301

<210> SEQ ID NO 34
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 34
tataaacatt tagattttt atataagaaa ttattctcaa gaatccactc tgtcatgtca        60
gcttgtttca atgcaaaaaa aaatattaag gaacggtttc ttaatttcca ttaagcactt      120
ggaaagaaac ctgcattgga gntggagatg ctgtaaggag tcactcttag gtaaagcttt      180
gtgtgaacaa tttgtgcacc anaaactatt tcccttctat atatatttca gaaaccaaaa     240
aacaatttgt gcaccacaaa aattaaacta ataaaaaaaa ttataaaggt ggtggaggng      300
t                                                                      301

<210> SEQ ID NO 35
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 35
gcatggttct cgacgtttac tgattttgtg ggttgtcacc ttgtggagga cccaccttga       60
ctgtgcttgt acgaggcttc tttctatttt gagcaangct aattaaccac acattattaa     120
aaaaaataca aaattttnat ggttttttct atttattta ataaatttta atcaattata      180
atagaaatat tttagaaaga atgagatcac tgggaaaaac tttaacgcat gaaagcatac     240
aacttcatgc gatatagctt attcgtggac caatattggg ttaggatcct ttcttcattt     300
t                                                                      301

<210> SEQ ID NO 36
<211> LENGTH: 1185
<212> TYPE: DNA
<213> ORGANISM: Glycine max
<220> FEATURE:
<221> NAME/KEY: unsure
<222> LOCATION: (1)..(1185)
<223> OTHER INFORMATION: unsure at all n locations

<400> SEQUENCE: 36
gcatcttgag caccttgggg nattggtgct gcggctgccg gtgcttatgc cttggnnnnt       60
nattatatat cttccttcaa taatatattt tgttcacgat cgtttattta atttgaaata     120
gatttatata ttacttatgt gagatgattc acaccccctt tttatatatt ttagctttaa     180
aatgttacct tcaccagaat aaaataaaga agtgcaaact ctttggtaat cgagggaaat     240
atatatacct cccccacata tacatcatca cttagacttg gacgtatcta aatcggttaa     300
```

```
ttttaatatg tttatatgta tgcgtgtgca ttaataattt tcatattttt ttttgtaagc    360
attttaaagc cttacatatt gaaaaaattg tcattaattt gtgttttgga catgaattaa    420
tcctatcatc ttgaatcatg tccacaaata atttcaattt gacattttct ttttaaggcg    480
gccaacatat atacatactt gatctttgta cttttggatt gtgatgcttt ataattgtg    540 gataatagat ataaaaatat attatagcta tatagtatta tttctctcta cccactgtgt    600
gtaactatac tgtctataca tctcatgtgg tttgttttt cttaaatgaa aattgttggg    660
gtcatgggtg tatagagtat agtactttta tgacgccatc agaagagaaa caataaaagt    720
tcataaaaaa ttaggtgtag aaaaagatgg aacttaagaa agaaaaaaga gagagagaaa    780
gtgattaagt gatgtaatat ataatgagaa atgaagaaaa agataggaag acaaataaag    840
taaaaaaaag aaagaagaa agaaagatat ataacaaaaa attgaaatgt atattctaat    900
atgtattgaa aacaaaattg atcccttttt gctgcaatgg ttaattttat gacagcatga    960
gaagcatgag gccaagaaag acccagagca tgctcacagg cacaaggtag aagaggagat   1020
tgcggcagca gctactgttg gtgctggtgg ttttgtcttg catgaacacc atgagaaaaa   1080
ggaagttaag aaagaagatg aggaagctca tggaagaag caccaccatc tgtttggctg   1140
aacatgataa atattcatat ataattaata ttcaagctcc aaacg                   1185
```

<210> SEQ ID NO 37
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 37

```
ctaatggtag aggaatccac gcattctagg aaattaagct ccctaccttg tgccatatcc     60
tcatactgca cctccacatt caacattaaa tcaacattta gccnatccgc aagagtaaac    120
tttgctctat tcatcattgc ntcaacttgt tccaattttg cattccacac catttcattc    180
attttcttcc aaatgttgca tatactcatg gccacaagat ctatcacggt acataactac    240
tggagaggat aggcacatcg cattgcacaa cgcagagggg ttcttgttaa ctcaacattt    300
g                                                                    301
```

<210> SEQ ID NO 38
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 38

```
ctcctctcct cattagttgt agccctctaa gctctaaaaa ctctctcctc tcatgttcca     60
caacttgatg aaggaagagt tcaagacttc naagttagtg atgatacttc acaacaatat    120
tattcacagt tcaatatgtg atatcgtaaa cttgtttcga cctttagcaa catcctacct    180
taggtcaatg ttggtcgacg atgaaacctc actactacaa aatcattttt ttacgacgca    240
nattntaaga ctgttattaa taaccatctt agaatgtgtc acaatgacat ttttgtaatt    300
a                                                                    301
```

```
<210> SEQ ID NO 39
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 39
taactaactc tcaacaactt aactgtcatt ctttctcttc ttattcttcc tactctacat    60
tagatgattt ctcttgccta accgtttttt ctttactatt ttctttcctt ccatccaaac   120
atacaattaa tgtgcatttc acttngcttt gaacaacact taaccgttta tgctagctcg   180
aagttggatt gaggtatctt ttacgttgaa cggggactga gctttaaatc caatctagaa   240
caaataatat tttgtatgta cgtattatta tatgaaaaaa aaggttttta aaagtagaat   300
t                                                                  301

<210> SEQ ID NO 40
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 40
cattcacaac aaaagccaaa acccttttag aggctcaccg gcgaagaagc tcaacaactt    60
ctctgatcaa aatcttcaca aaatctgaca cccttagaag caaagattga aactttntct   120
caaaatcaag ctgagaaccc tgaaacaaag acaaacaact aaaaagaaca catcctcagt   180
caccaaggag tgaagaagtg tcgtaagaaa acaagggaaa aagagaagaa aaagagcgaa   240
atcactaaag acaaggatta gtttgtgatg ngaactagtt actatgtaac naggctatat   300
a                                                                  301

<210> SEQ ID NO 41
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 41
aaaagacaaa gaaagaaatn atgttaagca tncaaaactt gatgtctaag tttatgttta    60
tgcttttgnc aatgttgaag tgaagctacn tgtaaggatg ttcacgagta tgagccactc   120
naattgaccc aaacacgttg gatgtttaat gtgttttagt tgagcccaaa tcaatccatt   180
caaactactt aacttttggg ttgtgtcaca agattttaat tcttgcactc actgacccga   240
cccatgaaca tctttttaat attaaattat tatatatata tatatatttc ataatatata   300
t                                                                  301

<210> SEQ ID NO 42
<211> LENGTH: 679
<212> TYPE: DNA
<213> ORGANISM: Glycine max
<220> FEATURE:
<221> NAME/KEY: unsure
<222> LOCATION: (1)..(679)
```

<223> OTHER INFORMATION: unsure at all n locations

<400> SEQUENCE: 42

```
ataatttgat catcatattc ctaaactttt ntgcttaagc agagacaagc tgctcaatgt    60
gtgggtcgtg taatccgttc aaaggctgat tatggaatga tgattttgc agacaaaagg    120
ttagtatcct tgagtccttt tgcttccatg aacatgttga acatttggga aaatgtgagg   180
gttgcttata gtattctacg ctgacgttaa tttgatgaag ncaacttgct agttctagt    240
tttgattcaa aaagcacaat gcactcttct ctttgtaact ttatggaatt tgtcctgaaa   300
tggattggaa gttattggtt gtctctaata atgaatgaca aaccaaaaga aacttgacaa   360
tcttcagaat ccagtttgtc aagcaaagaa agaaatatgt ttgttcaggt ccatgacatg   420
tttagtttca aaaaccaatg taactaacag atataannag caaaaattgg taaatgtctc   480
tgtaaatatc aataattaca gtcacaaatt ctatacattn tataggaaat anccaattta   540
aacttatgaa agtctgcatg aataaatggc ctatttacc tatgatgatt gctccattta   600
tggttttggc ttctactttt ctctatgaca gtgttctgac agtaaatagt aatacattgt   660
tggttataac ttctgcact                                                679
```

<210> SEQ ID NO 43
<211> LENGTH: 744
<212> TYPE: DNA
<213> ORGANISM: Glycine max

<400> SEQUENCE: 43

```
ctaagtacga aaatcgttat ccgccgcaac agccactaag atgttctttg agtcttggca    60
cgccacgtgt cagaactgcc aacagatagc cccatctctt tctccttctc cctaaacctc   120
gaactcagca cccccatcca ctggtccctc cccactccat catttattat actttcttct   180
tcttctttat tattgttgat taatataaca tacacccaca tatttcatat gggtacttgt   240
taatttgggt gtggattgtt agtttgttac ttgttttgtt ccgttcaggt gattgtttga   300
ttgagccttg aagaaatgga ccacagcgct gatgcacatc gcacggactt gatgaccata   360
acgcggttcg tgctgaacga gcaatccaag caccccgagt cacgcggcga tttcaccatc   420
ttgctcagtc acattgttct cggttgcaag ttcgtttgtt ccgctgtcag caaggtaagc   480
tatccctact ttgtgtgttt tttatcgaca aatattaatt gttagtatta ttaatccttt    540
ttctttttctt ctcttttcgt cattagacta atcttatatc tcgttatcat gtatttattt   600
cactctattc aaatatatta ttctggtctt aaatataaga agaagaaaaa aaatgattc     660
atgctgacta agaatgaaat attgattaga gttatgtgtt gtgacctgtg caggctggtc    720
ttgctaaact tattggactc gctg                                          744
```

<210> SEQ ID NO 44
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 44

```
accaagacgg tcatagacaa cgaccntcat tgtgttcatt caatttattt acaaaattgt    60
cattangtgg cattctagga cggttcttta tgatggtctt aaaacctctc acgtaaataa   120
taattataat nncattaatn acaanaatgt cactatgtta ttttctaaga aggcggctct   180
```

| | |
|---|---|
| acaaaaccgt cttagaatga ttgtcgtaga acgtaacttt tctggtagtg tctatctcaa | 240 |
| tggcaaccaa ttattagaag gnttttttgcn agaatctttg tccaattgca attatntgca | 300 |
| g | 301 |

<210> SEQ ID NO 45
<211> LENGTH: 766
<212> TYPE: DNA
<213> ORGANISM: Glycine max
<220> FEATURE:
<221> NAME/KEY: unsure
<222> LOCATION: (1)..(766)
<223> OTHER INFORMATION: unsure at all n locations

<400> SEQUENCE: 45

| | |
|---|---|
| attgcactcc gtgtagttgg gtccagaaga agcatttaca gaaacttcca tgtattggct | 60 |
| ataggcatgt agagcaacgt tgttcatcgc ttcaaatttt ttaatgtagg cttttggtat | 120 |
| tgggccgctg aagttgttgn aagagacatc aaaaatgact aaacngggga atccatgctt | 180 |
| gatcttttaaa ccggcaatgg gaccgtacaa cttgttggct cgcaaaacca atactttcaa | 240 |
| ttctggtaga gtttgaagcc aatggggaaa cacatccttt atttgattgt ttccaagatc | 300 |
| taaaacctcc agatgaatgc aattggacaa agattctggc aaaaaacctt ctaatanttg | 360 |
| gttgccattg agatccagag ttctgagctg acagtccttt gaaagatac ttggcaaagt | 420 |
| gccatgaagc ttgttcagtt gtagatccaa aactagaagg gatnatgagt ttgcaaggca | 480 |
| ttgtggaatg gttcctgtca acttgttgtg agacaagttg agaatctcaa ttgcacttgc | 540 |
| attgcaaatt gaggaagaga agtcaccagt gattgagtta aaactaagat caaggtaacc | 600 |
| gagttgttgg ttccatgaga attggtgcaa tgattgtgtc aataggttat gagagaggtc | 660 |
| caattcagat aacgatattt catgcaacca atttggcact ctacctttaa agttgttatt | 720 |
| ggacaaatag agcgattttc agattgggga cttttttcccc ataatt | 766 |

<210> SEQ ID NO 46
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 46

| | |
|---|---|
| atttccattc aacaaagtga atagtatttt ttacaaatta taattaaata tcaatanaaa | 60 |
| gattgctata ttacaattat acatcattgt ataatattaa aatatataat aattgaatta | 120 |
| ttaaaattac atatatatat atatatatat atatatatat atatatatat atatatatat | 180 |
| atatnttgct gaagcaactt tacctcttca cactttctct ataggtac aggtgttctt | 240 |
| cgtgtgtttt ataaattgga cttttnttaa gntaccgtac attaaaagtc gttatgatga | 300 |
| t | 301 |

<210> SEQ ID NO 47
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

```
<400> SEQUENCE: 47
tttcagtctt tattgttttc ctttattgtt tnttttttact actttgatttt cttgttttca    60 tttcatatac ttttcattta tatttccaac ctttgtcttt tacacaaant cntatcttct   120
acattcttct tcattcacct aaacctaatt tcttttagga gtaatttgag aacccatcat   180
aatcaagaag catattcccc tttctttgca cnaatcnttt gattattctg gccttttccag   240 atcttgttga gactagggaa aacatatttc gtctgatttt gaattttttaa gtgacatnaa   300 t                                                                   301

<210> SEQ ID NO 48
<211> LENGTH: 533
<212> TYPE: DNA
<213> ORGANISM: Glycine max
<220> FEATURE:
<221> NAME/KEY: unsure
<222> LOCATION: (1)..(533)
<223> OTHER INFORMATION: unsure at all n locations

<400> SEQUENCE: 48
attgaaaatg agaccagtat tcattnacaa gctgattgaa tagcgatcct tctttcttca    60
tcaggcacat tggatcatca tactccacca attttcctgt caatacaagt atcccttga   120 agaaaacaag taatagtaaa aaatatattct tcacctttat tctaatnaaa attcaacagt   180
gaaaatcaag tacccaatat tttacaagtt atcactaaat caactaattg tctattataa   240
taccctttaa ccaggtgaat gcaattaaat cctctgctaa acaacataac atgcctatct   300
atggggtgtg tcaaacccag tggtataggt agaaatagtt aacataacca taagaaaatg   360
gaattagagn tatgaattag cccgaaaaag gtttgttgaa tgacataaag gagtcggaaa   420 tatgcattt taccatctct gattgaaaga accatagtgc aatccatcac ggttggtatc   480
ctgtgtgcta ctgtgatcac tgtacaatct gcaaactcag tcctaatggt ctt          533

<210> SEQ ID NO 49
<211> LENGTH: 301
<212> TYPE: DNA
<213> ORGANISM: Glycine max

<400> SEQUENCE: 49
gttcacaagc gctgttggag gtacatacca aatgtagtaa aagcattaga aagctcaaca    60
aacttaacga gctcaacaga cagtggctta aaagttgaaa ctgaagcaag ttgatgcttt   120
ctagtgactt tgggtattta ggtcatcgac attataccat gccttagagt tgattttcaa   180
tcggcattgt tgttttcgac tatggttgca tttttttagtc gaccatgaaa tgtgctctga   240
gggagtaatc tagttggatt tggttctttc tttgtgtttg tctttgaccc atattttcga   300
a                                                                   301

<210> SEQ ID NO 50
<211> LENGTH: 301
<212> TYPE: DNA
<213> ORGANISM: Glycine max

<400> SEQUENCE: 50
atcatagtag gatcttgaag ttcaactgaa aatagataga gagaaagaga gaatttaccc    60
aacaaaagga gaaaaacag taaaaataaa aaagaagaa gaagaagcaa aaggaacgtg    120
gagtcccgtt tttgttggtt gggtttatga gggaattaga ctgaagtgtg aagccacgct   180
agctgctaca attaaattca tagtgatcat tagtcatata ttggatatct atcttgtact   240
```

```
ttgaaatgac atttcaagaa gctctgaccc tattttctct cacaaagctg ccatcaagat    300
c                                                                    301
```

<210> SEQ ID NO 51
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 51

```
tccacttagt taatccagac tgtcgatgca tttaacaaac aaacaaacat taaaagccat    60
aactgaaggc caacactata taaagggtca ggatgcatac tttgcaaagc aagcatagag   120
cataggtcat ccaaacaacg actggtgcag cacactgaca gaagatggga acttcagcag   180
ggccgaggca ttggcctcaa ctcatctata cgttggcatt tgcctaatt  gctgtcagtg   240 ttgtcgctgg tcatgataat ccttactatg cctctccacc atttaatgaa gaactcccnc   300
c                                                                   301
```

<210> SEQ ID NO 52
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 52

```
aattggaata gcgtgcaatc ttattgggtc ttactcaaaa aaataaaatt gggtcttaaa    60
tagacgtaag attgatttat aatgcattta atattttac  atttctcata catatanatg   120
tgagctttga tgtccaaaag gtgtttcatt ttccaggtca tatatgtgaa ctgtatcgac   180
ttgagattga tacatcatac ttcaatttgt ttgaggtttg acgtgttgcg gtgtgaattc   240
aacagagtcc taagtggaca taacactgat tcataacgta agaatttaa tattttttaca  300 t                                                                   301
```

<210> SEQ ID NO 53
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 53

```
caccncaaca caagacaaca aacacccttc ctttaataat agctagtgat gaggtgaatt    60
aatttcactg ggcatggttc ataaatacgc attgcttttg gaagaaacta cacaaagtag   120
atggctcggg aaatgaagca atagctggat gttcccagcc tctggttgga gtactttttac  180 cctcattcat accattattc tcattcttct ctgatgttcg aacttgaata gtgatatctg   240
cataaattgg ctgtggagaa agaacgagtg gagataacaa tggtattgcc cttgaagcct   300
c                                                                   301
```

<210> SEQ ID NO 54

<211> LENGTH: 492
<212> TYPE: DNA
<213> ORGANISM: Glycine max

<400> SEQUENCE: 54

```
atattgtggc tgcattgtct ggcatgaatc tgtcagctga tgatgtgtta gatggtgata    60
gccatttccc gtcacaggtt gagtcagatg ttgataatca tcagagatac ctatttggca   120
tgcaaggtgg tcaggatcct ggcaaacaac atgcatactt aaagaagtct gaatcaggac   180
acttgcataa atctgcttac tctgattcag gtaagaatgg tgggagtatg tcagacatca   240
acaatccatc tttggatagg catgctgagc tacaaaagtg tgctgttcct cccaataact   300
catacttcaa gggatcacct acctcagctt ttagtggtgg aggtggcgtg cctgctcagt   360
actcgccctt agatggtact aattcagcat ttacttacta tggcctgagt gggtacgctg   420
gaaatccagc attggcatcc ttggtggcta gccaacttgg aactagtaat ctgccaccct   480
tatttgaaaa tg                                                      492
```

<210> SEQ ID NO 55
<211> LENGTH: 586
<212> TYPE: DNA
<213> ORGANISM: Glycine max

<400> SEQUENCE: 55

```
tagttcattt gaatgcattg aaaaagtaca cctatgggaa gcatattgtt gctcgtgtag    60
agaaacttgt tgctgctgga ggtaattatt tcttgcttgc attaccgcta cattctctga   120
atatgtgcat gaataggaga tacacacctg aactaccctg ccaattatat gcctttagtt   180
gcatacttta ctgtttactt ttgatctgct aaggtattac gttacattac gtgtagtttg   240
ccaactgggt catgtaattt gttgcagaga ggagaattgc tgctcagtct cctcatcctg   300
cttaggtggg catagaaagt tgtttgtaca gctaactgag gctagtgtga gctttctcct   360
ctcttttcct gcatccggag gttatgttta ttcctatctc aatctgtcgt gatgggtagt   420
ggccgattgg aaataaaaac actatcggtt ttaatgaaga actgtacatt ttgtagtcca   480
aagtttatac atagaagaag aatttaagtg aggcgaggct cagatgtgta atactcacct   540
gatgcccccc tgcagcagag gagataaagc gacaatacga gccttt              586
```

<210> SEQ ID NO 56
<211> LENGTH: 121
<212> TYPE: DNA
<213> ORGANISM: Glycine max

<400> SEQUENCE: 56

```
aaataaccta catcgtttgg aatattatgt cttaggttac atcaagctca aattaattaa    60
atagacctat ttgataaata cgtgtggctt gggcttattt taaaatttat tcattttaaa   120
a                                                                  121
```

<210> SEQ ID NO 57
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 57

```
ttaatgtaac angcataagg gcaaccagcc aagctagaca acctcaacca ggctagctca    60
```

```
attacttcaa gtcagattaa aaagatataa attggtaggg agaaaaccaa agttttttgga    120 attgagtttc aaaaactgta tttagttttc aaaatccaac taaactaggt tgcttagaaa    180
actggtggag gggtgtgcaa agcatagagc agaatgtgca attgagggag aggttgaaca    240
aaataaaaac atcttctagc tatttcngtt ttatggtctt taaaacactt gttttttggg    300
g                                                                    301

<210> SEQ ID NO 58
<211> LENGTH: 895
<212> TYPE: DNA
<213> ORGANISM: Glycine max

<400> SEQUENCE: 58
ttcggactcg tacgggggac tctaaatcg acctgcagcc gatgtaaaga tcatatccta      60
tctcttttta agttttactt gacctagcta accatggcat attttgggca atgacagcgt    120 attttattatt atgagctata gatttaagta gtttatagaa cataaatcca aacaatttgc   180
tcagatttct aatatatatt acgagattag aagcaagcaa gtctacaatt atcttagcga    240
gtgtttggaa ctaattccac aacgcacatc atatctacta gaagcaacaa gaagtaattt    300
ctgcatcata tgggcttggt gacgtgattt ttataggacg caattccagt ggaaattctg    360
aatatacaag cagtcaattt ttatagcatc taaagcgatt cagtaaagcg caacagcaaa    420
acaccagtct tatatcattt atcgcttaat ggtgaagctg aagaactcta agaaacgca     480 atgtgaaaat agaatattta cataaataaa aaggctaaat tgtttctttt gccccctcaa    540
atatgagaca agaatcagtt taatcccata acatattgaa gtcaaatcat gacgggtgca    600
cagacgatga ccgtctatta cttccgctc tccttttct cttggctgga aattgtggcc      660
aaaatacaat attttttttc ttgtcaactc gaatggagta agatgggatc aaatcaaatt    720
gacaatgttt tgtgggatac aaaataatt tacaagttac aaccacacac gcaagaaaag     780
aaaagtgaag aatgggacta aaacgaaact ggcctaatga ggataaaaaa gaacacttca    840
gtccaaacca ataataaaaa gaagcttcag gttagcaaag ccagtcttga tggca         895

<210> SEQ ID NO 59
<211> LENGTH: 484
<212> TYPE: DNA
<213> ORGANISM: Glycine max

<400> SEQUENCE: 59
tggaaaacga atcaagcgtt gaattggttt gaatttgcat cccaatccaa ccaacgtcgc     60
aatttcattc ttttcatcca ataattcaat tcaccaatgg agcttttgaa gcctttgcac    120
cctcaccatg cacccatttt gcgaattccc tttcacgctg ttccctcctc ctcttcttct    180
tcttctcaat ctaaggttcc ccttcctatg atttctaagg ttcatgtagc tgttgggaaa    240
tcgctcgaca aagctgtccc cttgcttcga tggactttaa atcacttccg gaacgcggaa    300
atcgtcattg ttcatgctta tcaaccttct ctcaccatcc ccactctatg taagctcatt    360
tcattcaatt ttgattctga attttcatga tctccacttt ttccccccctt ttgcgctaat    420 tgattggatg tatttgaatt ttgtgcgttg aacagtgggg aaattgccag catcacaggc    480
tagt                                                                 484

<210> SEQ ID NO 60
<211> LENGTH: 1056
<212> TYPE: DNA
```

<213> ORGANISM: Glycine max

<400> SEQUENCE: 60

```
aaagaaatat gttctgcgta agggtcgtga ttcagagtat gcatggcatg ttgtccaaaa      60
tcatgcagac aatgcattgt attgtgaaac acctgccagg gcttttttaga aagtgaatct    120
gggcattttc ttagatgctt gtgattgtct tttaacataa ctgaaaagaa ttgtatatat    180
ccctttttaac acttttcata ggatccctgc tcacctaacg cttttgatct tttggccata   240
atgcattact aacaacactt tcaacattga gtgcccatat taataattga cattcagtat   300
ttcccttgct tttccattaa gtacctgata tcacatcctt atttcctctc tccgctttaa   360
ttttaaataa ataaatccgt tgcgaaccac ttggataaat gagtataaaa tctggagaaa   420
ctaggcttgc atgtagatta ctagatttct cgtttgtggg gttttaaata cgtatgcgta   480
agtgatggca atactgctct aaaagtgaa ggctctactg ccgccacctc cttcgtggag    540
cagcacaatg cctccgcaat tgctccaaaa aggaagaaat attgaattgc tacttctgaa   600
tcgaggacat caaagtcatt acgatatgac aaatgttaaa ttaagaaatt taagtaaaa   660
atattttat tgggaaatac aatattatat tattcattgt ttttttataa tttatataat     720
aaatatttt ttaatttcct aattcatgtc ctaaaaataa tttaataaga tccataagaa    780
attagtagtt ttttcttaat tatgaccggt tagtgtaacg acacaatgat tctgtttctc    840
tttattgtcg acagagctat agaaaaagct gatgagcatg gctattggct attgcaaatt    900
aatgataaag cattctcact cgttatgtca ctctttttga ccccattctt gctctaattg   960
gacttggatt ttaccaacag cgtctcttta ttcacagttc ttggcaataa ttctcagttt  1020
ctatgcattg cacagaacaa caaggagtgg acgatt                             1056
```

<210> SEQ ID NO 61
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 61

```
aagactgcag catgtcacta caaattttgc tgtttgtaag acgattgaat tgaaattctt     60
tcctttattc tggttatctt ttcaactttc ctttgttaag tgtctttgag aactgagctt   120
gaggaatttt aattacatag tccggaatca tcatgccatt tactctgatg caaggtgtac   180
acacaagtga tgatgtgaaa ttgattcaca atatctagtn gaattttgtt tngaattgta   240
taattcanct tgtctggagc tagaactaat ctgtagttag ttttacatga ttattttctg   300
c                                                                   301
```

<210> SEQ ID NO 62
<211> LENGTH: 301
<212> TYPE: DNA
<213> ORGANISM: Glycine max

<400> SEQUENCE: 62

```
tataggatcc aaagctagat cagctgaatg ataagggcag agtcagcaaa agggcatttg     60
agaagagaga gaaagcgcaa gacaaacaga aacacacctt gggtaactag tccgaatgga   120
gagaacaact tcttgagctg ctcctgtgta gtgtaaagca taatcatgaa aaatgaaatg   180
aagcaatggt gagagagggg ttgggcttca atttattgaa gagagggagg agagaagaac   240
```

```
cctaactgtg gacgaagagc tttgtcccga ttctccgtga catctccact ttccgattga    300
t                                                                   301

<210> SEQ ID NO 63
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 63
aatatatttt tggtgataaa aatganagtg gaaaatatac aagtatgtca gtcaagttga    60
atacggctag tgaataattc aatgaacatg anagatatag gaattattaa agatacaaga   120
ataacaatta ataattcacc taatatattt ccgaaaatgt cttacccctc ctaataaatg   180
tggctagcta gcaatagaaa atttgtaata caaataagga taaatagtna cttttgtttc   240
ttgaaatagt cacttttgtt ttttgatgtg taattcattg ataaatacat ccctaaaagt   300
g                                                                   301

<210> SEQ ID NO 64
<211> LENGTH: 301
<212> TYPE: DNA
<213> ORGANISM: Glycine max

<400> SEQUENCE: 64
aataaagaaa acaaaaaaaa atattattat agtagtagta taaattagtg tttgaattgt    60
tatctgtatg actgtatcat atatttaatt atatccgttc tcattatata agagttatat   120
atattgtaat atctccctcc ctccctcgaa agctaaacgc ctacatggcc caactctctt   180
cagagtcaac gccacctaaa tctaaacgtt attttctgta gcacacaatc agacagcaac   240
cctttcatgt gtgctgcaat cccatgatta aaaattggcg gtcaacggct acgctctcca   300
t                                                                   301

<210> SEQ ID NO 65
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 65
gncatggctc cctggngtta gaggnggngg caatctcgtc gacccagaat ggcttgatgg    60
atcgtgagtc caccnaatt ccttcccnct ttttggtttc aaaatgtgtt ttctataata   120
attccatgca tattcagcaa tccatttgtc atattctgaa aattgtttct aaaattaagt   180
gttttgtggt ctgagcttac tggtgtgagt catctgtatt ggtgttgaat atggtcctaa   240
cttaagggtg tgagtcattt gaaatgatgt cgaanggtga ggcatgaact tggtttagtc   300
t                                                                   301

<210> SEQ ID NO 66
<211> LENGTH: 301
<212> TYPE: DNA
<213> ORGANISM: Glycine max
<220> FEATURE:
```

```
<221> NAME/KEY: unsure
<222> LOCATION: (1)..(301)
<223> OTHER INFORMATION: unsure at all n locations

<400> SEQUENCE: 66
aggtatttat aagtgtggtt tagtcaactt tgggtatct caaaaaaaca aaagtcaact      60
tttggagaaa gagtaagcaa agccggctac atgcaatgca agtgtattga aatgatgata    120
tggctaaggg ttcacataca tatgaaaccg ngctcacggg ttttgtcttg tgccgaggca    180
cggtctactg tgatgcngct agtgcaaata aaaatgatac cgcgtgagag tgtgtattta    240
gtcaaagttt tccattttgg tgaccaccac accaaaaagt agagctttat gcgggaaagc    300
t                                                                    301

<210> SEQ ID NO 67
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 67
atatggaaca taccctttnct gactcacccc ttatgtgcac aaagcattat gattcaagct    60
ttacaaaatg aaagaattct aaatctctgc catttcaaat tccttgcaat ttgaaatttt    120
ctcatccaaa acacaaggta aagacaaatg tcaaatttta actgttatac cggtacagct    180
ggcaactggc acctgggaag agaaataact caagttgaag ctaacaagct ttaatttgtc    240
cagaatttca tgatgaaact caaatctttt gttaccaaat tcagtttata gctgtagtt    300 t                                                                    301

<210> SEQ ID NO 68
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 68
atttaaacat aaacatggca ttaatgaatt actaacactg gggctcggct atacacaggg     60
aaggaaagag aaaaagagag agtagattaa tcgataaaga gaaacaaaaa gaaagaaaa    120 acaacatagt atgtagatac ccaaatagca tgtggaagta agatttagtg gccagctgac   180
cacgtgattt ttatattgct atagactata aataagtgcc cactagtgtt tgtataaact    240
tatgtattaa tattaantca tgcatggagc tttaatataa gctatcggct gngtttatga   300
t                                                                    301

<210> SEQ ID NO 69
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 69
tacggccaga ttctgaaagc tgcttcctag aaagtaccta ttgcttttat tcacggtctt     60
```

```
cataatcact aagtggattt acttcggata ttgtctggta ataattatct accttgggga    120
ttttgctgtt gaaagancat catgatatag atttaattaa atagtattgc taattaatgc    180
taatgtttgc tttggaccgt acaggagaat ttcaagtagc catcaaaaca gaaccggagt    240
gatggtctct ggtttatttta taatggaagt tggcggtacg tcaaatttgg cttcttctat    300
a                                                                    301

<210> SEQ ID NO 70
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 70
ttaacttttt catttttatt taatataaaa tttcacctca aacttataat tcaataatat     60
aagcttgtag gcaaggttac ctaagtgaga tnagttcata ttaaaagtgt gaatatattt    120
cagtgtgttt gtcggaaatg aataattatt ttcctttcct agttaaccaa ttgctcataa    180
caaacttttg ttcgtttggc aaaactcaaa ttgcaacata ttccctcatt ttngttaaaa    240
gagaaaattg ccatgaaaca gcttgaaaat tgaatacaca aagggagact atctagtatg    300
t                                                                    301

<210> SEQ ID NO 71
<211> LENGTH: 1102
<212> TYPE: DNA
<213> ORGANISM: Glycine max
<220> FEATURE:
<221> NAME/KEY: unsure
<222> LOCATION: (1)..(1102)
<223> OTHER INFORMATION: unsure at all n locations

<400> SEQUENCE: 71
gtttcgccag cttgcactgc ctgagatgaa gtaattgctg ctgcggtgct gctccggcac     60
cgccttgtgc tggtgcccgg ccaccaggta gagcaaaaga tgtcactcac tctgttcatg    120
aaaaatgggc tcaaggtcaa tgtgcatgag agggatttga gaggggttat cacaagtatt    180
aaaaaggaaa gggaggaaga tgttgatttg agaagtaacg aaagttagtg tggtgttcaa    240
tagatgaagc agagggtgtt ggaggttttt gaatgtggag acaagttcaa atgagaaaaa    300 ttcagacccct gggctttag cttatagaac aagagaaaca aatttccttt taagaaaagg    360
gtatattcag agtatttata attcttatga taaattgtgg atggattctt tttccagggt    420
cgtgggatgg atgattgctt tctcaatcca tcgttccttg tagaatcctt gcaaatattc    480
attgtattct ttatttcttg tcggttttga tgtttctatt taatttttact ggtggtgaga    540 gctaaactca catttcacaa tgttaatgt tgatgttcat aaaagaatgc cttacgtttt    600
atgaaagtat aatgatcgga tttgactctt ttgtcatata taatggatga tgcttaagtg    660
gtagtggtat actcaaaaac tgcaaaattt agctttacag ttcatctgca ttttttggtg    720
aatattcatc tgtgatttta gattctgttt ccaggatcct tgcctatgac aatgaaattg    780
aaatgcacan attgaaccag tagtaaaagt agatatactg atgtcttttg ttaggggaca    840
ttgaatcaga aaactgtgcg accaattttc tcagccatgt atgatgaaga agcagagttg    900
gccatataac atgtatttta actttaagca taagtatgct tgagttatat aagtggacat    960
```

```
tatccaccat ctatacagaa accatttaga tcatgggaca agacatttgc aaaaggtgcc    1020
tagttaatcc aagatttcta gataaaatgt aaaggctttc agctatttga tcaaaaactt    1080
tgatggttgc tctcttcgat tt                                             1102

<210> SEQ ID NO 72
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 72
tattttaacc aattagcata agagacaata aaaaataact ccataatatt aacaagattg      60
tgacttaagt tgcctatcca caatttgnaa ataatttat caaaatgcaa gcacaaaaat      120
aaatttacga aattgaacaa aatgcaattt ttaaggaaat aaacattgaa atgctatcct     180
tggattagtt ttaaggctct agtggtacca taacttgatg tgccgcacgc tcacgtattc     240
tacaattcgg ataagaggta tagactatag agaaatattg tctgattttt agtttctctc     300
a                                                                    301

<210> SEQ ID NO 73
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 73
aaatcacact ttactctcaa gtgcactttt gcactttata atatccaaat tnatatataa      60
tttttccccc acttagaaga gacgttaaat gatgtcagtg ttgtcaactg ggtactctaa    120
ctttaatatt agtctgtttg gatataagtc ataagctctt ttgagagttt ctctactaaa   180
aatataccat tttcttgttc tcatgccttc ttcatgcttg aacttgaaca tccctttaac    240
aaatgcagga agaagtgcta gttaatgcct ccgtggtgaa agtggaaga aaattgactg      300 t                                                                    301

<210> SEQ ID NO 74
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 74
tttgcttnca ttttacttag ttattacttg agattttcta tgaaaatgca tgttttaaca      60
agccgatgat ttcttcaatt gcttagcaga tatantnatt gtcataatgt taagagtagc    120
tacatctttt caacaangtt aaaatgcact actaagcatt taaacacaca ttagccaaca   180
agtccatttt ctgcaatgtc ttttccaatt taaatgactt ccaaaacata tgcactcatg     240
ctccaaatca agtaaaaata tcttcaactt tttttcatgt atatacagac agagaaacac    300
c                                                                    301
```

```
<210> SEQ ID NO 75
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 75
tagtgaaata cgtaatgcgt tagttgaaga gaacaaaagn ttacatgttc anatatcaaa      60
agtctaacaa tttggctaca tgcccaacac gttatgcant ggagatgagt gtactataaa     120
gggaaggcca atgtatgcag gtgtattcaa tcaatgtttg tcaaatctgg tgagctaaac     180
tgatgttggg naaattttan agaaggaggt tgattttgtg gttggaaaag aaaggtttga     240
aggacggagt gagttcaaat tttatcacta atattttaat aaaaattaat aattaaagtt     300
g                                                                     301

<210> SEQ ID NO 76
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 76
ttaaaataat taatatttta tgtatgcaac cttanttaac ccccaatgtg tttctttcct      60
tgggtgtgac tcgacctaag tcagtgagtc actngactaa ntgcaaacnn gattgggtta     120
cactaagttt aacgcttnat caatctgata ggcaactcga ctcagtcaaa cttttgagtc     180
gcagtcaaac cagttcaatc agttgggttg gtctngattt taaaacatta tcaccaccat     240
cactattgtc attactacta tttcaccccn accactattg tcattgctag caccaccatt     300
c                                                                     301

<210> SEQ ID NO 77
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 77
tcttcataaa aaagacatcc aaanaataaa ttctagatga tagaaattta aattntatga      60
taaattattt tncttaatta aaattcttta tccaaataaa ntctagatat tttngggaga     120
aaggaaatga tttatttcta ggatagagat agtgaagatg gtcctcccac atgtgattct     180
aatttgggct catatgtagc ttttagaatc cacgtcttat cctttttgtcc attccatctt    240
gctacttctt cctcttgaac tgacaaataa cattcttaaa gagcagcata attcttcaaa     300
c                                                                     301

<210> SEQ ID NO 78
<211> LENGTH: 301
<212> TYPE: DNA
<213> ORGANISM: Glycine max
<220> FEATURE:
<221> NAME/KEY: unsure
<222> LOCATION: (1)..(301)
```

<223> OTHER INFORMATION: unsure at all n locations

<400> SEQUENCE: 78

```
aggcaactta actaacaaaa acaaatttct aaagtaaaat cagaaaacac aggtagcaat    60
tctgagctta accataataa aaacaaggaa taaataaatg gagtcattta cgaaaattcc   120
tttattgtta atatgaaaaa agaaaataa atttctgata gaaacaagtt actaatacta   180
tgaacagnaa caaatgtgag aacacaagca cacagtacac acatggcatg tgcgcataca   240
tttgccaatg tgagcttata gccttctact ttacaggcac atcttcctag agacacatgc   300
a                                                                   301
```

<210> SEQ ID NO 79
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 79

```
gtggatgcca tgtcaaaaga aggtgtttca aggatgaatt ttaaaatttt catattcctc    60
ttaaccacat gaattataag attccctcta cgggtctgaa ctanaaantt tttcatattn   120
cttgggttga ataaacctga ctacatttaa aaacagccat cacgagccaa cccttcgcta   180
tgagcctact actgtaataa ttaagaggat tttccaaaca aaaactaaaa attttcacgt   240
tcaacaaagc aagctagcta acttgaattt aaattgatgc agtgtaacct tctataaact   300
a                                                                   301
```

<210> SEQ ID NO 80
<211> LENGTH: 301
<212> TYPE: DNA
<213> ORGANISM: Glycine max

<400> SEQUENCE: 80

```
aagtgcattc ccctcatatt tctatcgacg tgggactcca tgataggtaa aatgatttaa    60
taactgataa ttcaagcctc agtgcaggac atgagggtat ctatcgatgt gagacttatt   120
tagagaactg ccattgttaa actgatgata tagatgtggg actacttctt atgcctcaac   180
atgatgtggg agtgggacta ttgctagctt aatatatgct tagtttaaat cactactcac   240
aattaaaata gtccttgcaa tattcaatat tttagctttg gtccttgttg ttacttaatt   300
t                                                                   301
```

<210> SEQ ID NO 81
<211> LENGTH: 301
<212> TYPE: DNA
<213> ORGANISM: Glycine max

<400> SEQUENCE: 81

```
caatatggca tgtttatctg gtaagcgtag ataattagtc tgaaactgac actcaaaaaa    60
ctttaagcca acgttatgtg aaccagtcaa atcagtatca taaaaaaaaa cagtcaaatc   120
agtagggacc aatcctagca aattagacca ccaaaaggga ttaattacaa aggagaaatg   180
attttcttgt aattaatatt ccaactaata tggcattgaa caggaagcta gagaaacatc   240
ctaatgagga aaatagtagg gcaaaacaaa ataaaaataa tgcccttctc tataacagaa   300
t                                                                   301
```

<210> SEQ ID NO 82
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 82

```
actttgtcaa aagaaaagc tttcccatgc ctgcattgga aagactaaga gaaaagnagg      60
gttagcttgt gtgcaagtta caaattttac tcatacattt agtttgcatg atgagctgta    120
caattaaggg ttcagataca tattggcaag tggcaacaaa gggaagttgg aagtgaaaca    180
gctactattc tcatcgttcc taaaatgttt ctttcattta acaaaatgaa tttgcaagag    240
taaacatatc acagaaggca ttaatcaggt gccataatca gggcagagaa taattttaat    300
g                                                                    301
```

<210> SEQ ID NO 83
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 83

```
aggtttttgg gcttagcgca cangtgtgcg ctgagcgagt tatgcaactc ttattggcct     60
gcaactttcg ttaagtagga catggctcac ttatcgaatt aaatgcctca tgatgcagta    120
gaggggtcac gcttagcgag atgggctcgc ttagcgctat gccattttag agagagttat    180
gggcttagcg ggtatggtac acttagtcca atagccatga aaatccaaga agagagcctt    240
ctacgcttat cgcatagaca cgcttagcga gagactatgt cgcgtttagc cctattccat    300
t                                                                    301
```

<210> SEQ ID NO 84
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 84

```
catantctta attcgaatgc tattttcttc tttgaaacgt tgntttattg taagagaatt     60
gaggaaataa aataaagtta ggttttgatt attttttntt gttgattgtt caggaagaaa    120
tgatggttta actttttttc tgtaggaaac ctttccactc tcaacttaat aggtactcta    180
gacaagccaa cttggagact aattggtttt tatggattcc cngagaaaaa taggaggaag    240
gattcttgng attttattga gaactcttgc ataggatcat tctctcccnt ggtgtataat    300
a                                                                    301
```

<210> SEQ ID NO 85
<211> LENGTH: 301
<212> TYPE: DNA
<213> ORGANISM: Glycine max
<220> FEATURE:

```
<221> NAME/KEY: unsure
<222> LOCATION: (1)..(301)
<223> OTHER INFORMATION: unsure at all n locations

<400> SEQUENCE: 85
ttggcaagga cctattttga gtctctctat tctcgtgatg acggggacca tgcaaaacta    60 ttttntttt  tttattcttc agtaaatatt agtttgaact tttcatgttt ttacaattta   120
ttataaaatc taattattta tataattaga gtaaaagtat tttcgtgtat gtttcacgtg   180
tgtgtagtga atcaaaacta acataattct acatagatag atagatagat aattttttta   240
cagaagtata cacatattta atctgctatt aatttatgta aagaatgttg cataaaagaa   300
t                                                                   301

<210> SEQ ID NO 86
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 86
catatcctgc aagataagat agaactggaa atcttctttt tcaataaata gcgatcaaac    60
aatgaactta aaaatccttt agtcttgttt atcttagatt tatgattaag ttagtgaagt   120
gttttaagat aaaatatcaa acttattgga attgatattt ttttgggtat ttaattgagc   180 attttttacaa gacaacgatg ttcgggtacg cccaatgtgg tagttaagtt cttgaatttt   240
tggcagataa ttaatcatat acacngtcaa taaaaaacat ccttatttca aaaatatatg   300
t                                                                   301

<210> SEQ ID NO 87
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 87
tagaactctt tttcttattt gtcttgatca aagaatgaaa cccaatatat gtatataggt    60
aaatgctgtg gcataacata agaaattaaa gtgaaaaaaa taaaacggta atttcattt   120 caacgtaatg ctttattaaa cagaaaagaa gagaaccccn atctcctcaa ttatatgatt   180
aggattaggg cttctgcgtg tgtaattatc attcgccaaa aatgacatct ttgttaccca   240
gctattgcgg gaaatataga tatattactt atgagaaatt aaagctgcgt acattactca   300
a                                                                   301

<210> SEQ ID NO 88
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 88
gcgctggttn tcttcgcttg tacaaacgaa agtaattgtg attactataa aataggcaaa    60
```

```
taacaaatgg tcagtgatgg cctcaaactg ggatgcttgt caattttttgg ggcagggtct    120 ttcacatttg atgaaccttg ttggctatcg agcagggtat ttccaaagtt tggtctgcaa    180
aacagattac tgagaaacca tcaattngac caaatattta gatgtctatc ttcaagctca    240
aggagcgatc ataacagata tcaaatgtct tgaaactcat gggagttggt tactgatcac    300
g                                                                    301

<210> SEQ ID NO 89
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 89
tccttggtgc taccgtatac cattttgtat tttcaattta cagttgtcac atgttacata     60
aaattctgtt cctcttaaaa aattatttgt gtactgttgg tctattaaat tgtcatagta    120
tgtatgtatg atagttctcc taacaagaga tgcaaacagg ctagtaaaga tgcagcgagg    180
aggctgaaaa ttttgggcct agtcatcaca gtttagtcat gtttcactct tgggatgtag    240
tagtattaat taaaatgttc ttataagact tgaacaatcn ttcttaattc aaataaaaat    300
a                                                                    301

<210> SEQ ID NO 90
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 90
ttcccctatt ttttatgtag aaaaaatgta aatatgcact aaaaatttta ctattttcat     60
taaaaaaatt gataatttta attttaaact ttatacattt ttagtgcaca atgccactat    120
aaagtttgnt ttttttttccg tcaagggtgg ctgaaggcca tacgaacaga acggggggaat    180 gaaaccccta aaaaagttt taatctcaaa cttttacaac tagaaccacc ctaataggtt    240
atttaaatta ataaaatata ataaagttaa tatgaattgg taaacactaa ttaatgaatt    300
g                                                                    301

<210> SEQ ID NO 91
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 91
gacacttgat cgttaataga nanatatata tatatatata tatatatnna tagagagaga     60
gagagagaga gactttttttg agtaacttga aagggtgaca atgtaaaact ataagaggat    120
aatgtaccca aattataatt acaaaaggga gaaaatgaag atcacatcct tgaccaaagg    180
ggctatatac tgatggcacc atagcaatac aacatggtga taaaacatga cattttcaac    240
```

```
aaggcttctg aaattctaaa gaagtatttt cacactaaaa gaacaattgc gaatatttac        300
t                                                                        301
```

<210> SEQ ID NO 92
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 92

```
aaggagttga gctctggtaa ttaacgaatg caacacaana caagtgagtg aagagaaaaa         60
acggggttgg gttgggtgcg attctgaaan tgacggaaac gtcccattca cgccaacaca        120
ctcatnatta accaactaac ttcaactaag aaagtgaaac ctctcccctc cttacctttg        180
cttttaccaa tgtttccttc cccaaccaaa caaccacaaa tcttgtctcc ttacttccca        240
tttcttttc tcttttggt tttattcttt acaatatatt aatttaattt taatcttttc         300
a                                                                        301
```

<210> SEQ ID NO 93
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 93

```
ttactcaaat tttctcctcc tttagttagt tgaatncttt ctaggctgat tggtgattcg         60
gattcattat tagaggctcc acattggatg acagaggcct ataacacatg ttgaggttgg        120
ttcgaggtgg tgaatacata aaacatgatg gaatttgata actttaagtg gtaggggttt        180
ctcattggat gaaagaggcc tataccactt gttgngattg attgaaaatg gtggatacat        240
ataatgttgg aaaatttgag aattgtcatc ggtaagggat gattgatttt gcaaagatt        300
g                                                                        301
```

<210> SEQ ID NO 94
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 94

```
ttgcaatctg actcaaacaa tatgttgtta atattgagct ccctcctgca gcagacccat         60
tgctcgaata aattggccat ggtcatcacg taagtaagat tcctattcca aagcactgct        120
gctgttaaaa tatgttagca tcttgcgttt aatttcacct tttggagtgc tgcatttgct        180
gttgttggaa gtggcattat atatgattcg aatcatatgt tttgttcaat attttttatg        240
aaattaatct tntaaagtga ataaatattt ttaaataaaa atatatttac cattaattta        300
a                                                                        301
```

<210> SEQ ID NO 95
<211> LENGTH: 301

```
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 95
ctgatattag tggttactat cgacagccga caggcaaagt atcatcgatc cacaaccaac    60
tgaagaaaat aaaattagtt ttttttttat tatttacata agtaacaagg gaataacgat   120
aaaaagtaaa aaaaatataa aagaaacttt ccactacata gcctataatc tagtgtcatt   180
tttgggctct ctttccccac atctatcaac aacattgacc atattaaaac atantgttgc   240
aatgatcgaa aatgattttt ttcacaataa ctaaaaataa aagcaactat acctttcat    300
a                                                                   301

<210> SEQ ID NO 96
<211> LENGTH: 301
<212> TYPE: DNA
<213> ORGANISM: Glycine max

<400> SEQUENCE: 96
aaatagaaca aaatgtttta gagaattcag aatgagaatg ctttcttatt caagagaaca    60
tgaaatccat ctaggttaat attaattcag cccaacttca taaatactaa ttcccacgaa   120
cactaaatgc atcttatcat gtgatacata tactattacc tagtgcattg actcttataa   180
tttccagcag aaacagcctc accgattaaa ttcaaaatga tgctggtgaa gtaatagacc   240
taaaaattac taaggtaaag aaaaatacgt aaaacagacc agaaaataa aatacaaaga   300
a                                                                   301

<210> SEQ ID NO 97
<211> LENGTH: 301
<212> TYPE: DNA
<213> ORGANISM: Glycine max

<400> SEQUENCE: 97
gcattaatga aaaatggagt acacggaaaa gatcacacgc aaacaatatt ttgtcaagga    60
aaacgccata cctatacata cacagaaaat tcatatttga cagggatgga gaaaaacata   120
tctgtaccta cacaagggat agacaggtaa tcttccccca agcttcctcc ttcttcaagt   180
cttttttctct attatccggt atttcttagc cgggaaggca ggatacctgt caaaagtatc   240
ccaatgctca agttatatct cagacaaaaa aaatagaatg cgtacttaat gtgatgaaca   300
a                                                                   301

<210> SEQ ID NO 98
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 98
acgattattt atcttttctt tgggaacaag tcccttaaa tatttaaatt tctaatgtaa    60
aaaggtccct aatcaancat ttgttttaa ttttatagt aatttagcat agaaantcaa   120
ttcacaatt gctaggaagt tcttttaagt gaattaggaa cccaatngaa ggacaaaagc   180
```

```
ctccctcaaa tcaattgcta agagagaatc atctgtggtt aatccgttgc taccgctgaa    240
cagacgcaaa attcacacca acaaattcat acaaaaaaat atgaaagtaa agagacacaa    300
c                                                                   301
```

<210> SEQ ID NO 99
<211> LENGTH: 495
<212> TYPE: DNA
<213> ORGANISM: Glycine max

<400> SEQUENCE: 99

```
ggagttatat ttcttgtttt aagagcacca acaaagaaa ctggattctc cacacacgac     60
aatcttgttg atgttccctt tgaaaaaata tctaacaagc gttcattttc ataccaatag   120
gcagccatac tgaactttcc tctcagaatt atactttcca ttttcatacc atgggcagtc   180
atttgtttgg caatggtggt aacttgctct tcctttgttc cttcatcaga ttcttttgat   240
ggacataggg catttgtaat aagacagaga cgtttctttc ccttgtttgt cattccaaat   300 tttttatta acatatccac gccaacaatg acaacatcaa gaactaacat caaagtcaag   360
gtgatatgat cagggataaa acaagaaca atttagtaat tcctagcatt cgaggtctag   420
gaacctccag agaagaagct aagaaaggga agttttattt tctgcttgct tcatcacgat   480
acatcattca ttctt                                                   495
```

<210> SEQ ID NO 100
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 100

```
aaaactccga taancattan aaccggcgat aaaaatgagt gatcaaaact acacattaaa    60
ngcacttttt tttaataata aaaatgttag gaagaatgta cgtgatagta gtaaggaaga   120
aacaagatag ggctagcttc ggatgtacgg ccaagagtgg aatcttgttt tgcagctcta   180
tgaccagttt ggtttattca tcacaggaag gagaaatgga agatggaaac acttgctatg   240
gcatgctacg tgttggtgta tgtggaatgc taggaacaac atcgatatca tttgtccgga   300
c                                                                  301
```

<210> SEQ ID NO 101
<211> LENGTH: 301
<212> TYPE: DNA
<213> ORGANISM: Glycine max

<400> SEQUENCE: 101

```
ttaatattta atagattttg aatgagaaat tgattgctga gtactgtgag attgttttag    60
aaaacaattt ttaatatttta taaccaaaaa atgagaatgg aatcaaatag gccctaaatc   120
ttttacaact taatgaggac tatacaatcc acttgtttcc tcatgtttca tgtcgctgaa   180
gcatgtgacc aacttggtta ctgtgtaaaa ctcacttcac aaaacatgtc atttatccaa   240
atatagagga agatgttgaa cgctaatgtt tgtacagaaa ctgattctca aacttccttt   300
c                                                                  301
```

<210> SEQ ID NO 102
<211> LENGTH: 301

```
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 102
actgctcttt tttcccctac ctacctgcat acgatgttat ctacttctac tttacaagct    60
tcattgatct cacttcaact gcttcaattc agatggtaat aactaataac tctcgatcga   120
gagccaaata atgttttgag ttcagtttca ccatgcacca tgcccatctg ttttcgtaat   180
ttgatggatc taagaagcaa atttgctctg tttttactg tatacgtgac agagaagtaa    240
acacgcactt gatccaattc ctttcgtgga aatcaacagt antagcaaca ataaaacata   300
t                                                                   301

<210> SEQ ID NO 103
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 103
ttaaattatt aagaaattta tctttttttt tcataaaagt agttctaaaa aagcctatcc    60
aaatatcttt gttggtgttt ttactgacaa aggaatgcga agtttggtt gctttggatc    120 aattgaagta ataagccggg aagcttggtt tggaaagatc atgtgtttat cggacctctt   180
gtttgaaaac atctcatgcc aaatccaatt cacattgcag gcttagcgtg aaggagtcca   240
aaccacaatg gtgtttcgtt ttttgtcatg cttatcgctt gtttttgtat tggntttatt   300
t                                                                   301

<210> SEQ ID NO 104
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 104
ctaaaaagat ctaaattatc atttcttaaa atatctcaat taattcatta ccatcatgat    60
tgacgttatc attaccatga gcatccttgc attcatcacc ataaatcatc attgtcatca   120
cctctgtcac catcaccttt tgtcatcat cgtcgttgtc atcaactgtc accatcatta   180
tcgttgctat cgtcattacc accatcacaa caacaatgac aagatcatga cggtggagnt   240
gttgatcgac ttcaaaaatt ataagaatat ctttctaaaa ataactactt ataaacttt    300 t                                                                   301

<210> SEQ ID NO 105
<211> LENGTH: 301
<212> TYPE: DNA
<213> ORGANISM: Glycine max

<400> SEQUENCE: 105
tttatacact taacatataa ccaataaact cttatatatg taataaattt ttatttatga    60
```

```
caaatattta atataattat atatttataa tttaaatttg agttcacaag ttatattaac      120
tatcggttaa ttaaattaaa atcattttac actggttaat gcacacacta acaataataa      180
agttgataat cagattttt ttttcttaaa aaaaagaac gacaatatgt tgcctccagt        240
ccatggaaat gtggaattct tgatttgatt ggaagataac aaataaaata tgagcaatga      300
a                                                                      301

<210> SEQ ID NO 106
<211> LENGTH: 301
<212> TYPE: DNA
<213> ORGANISM: Glycine max

<400> SEQUENCE: 106
aaaatggccc aaatctcctt attttgcgaa ttaaataaca tcatctatga tttagcaaat       60
aaagaatgtg attttttata tatttttaat ggattaaata atgtgattta tctcctaaat      120
attattatta ttattattat tattattatt attttatgat agggttgggt actcacatac      180
ccataaccac catcgttttc attaaaattt gtggataatt agtgtacctc agctcataat      240
ccattaagtg gataattact ttatttatga tggataattt ttttgagtaa tagtagaatt      300
t                                                                      301

<210> SEQ ID NO 107
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 107
ttttctaaat tataaccaca gaagtgtcta atgcaaacaa ttngatttgc attattcttt       60
ttatttattt atttattaat atttgcatta ttcatatcaa ctacttctta gcataggtgt      120
caagataaat taaagtgttg gcgttgccaa cttcaagcag agaaagatca agtggccttg      180
actgtaactt tttgactgga tcatcaagtc tattattttg ggaatttatt gaaatatact      240
gataatataa ataattttta tattaccaat taattagagt ttgttatatt attataaaat      300
t                                                                      301

<210> SEQ ID NO 108
<211> LENGTH: 301
<212> TYPE: DNA
<213> ORGANISM: Glycine max

<400> SEQUENCE: 108
aatttgcagt tagtgctaca agagtgagct tcacgatgac gaggagtctc tcccatattt       60
gtcgttgaat atttgtgaat tgcggatcac cacacgacca tttccttccc tctttgttgc      120
cttcttgaca tcttttgttg ctgcaacact catttttttt caattaacct tttcttcctc      180
aacgaagttc aattcttctt tcttttgcac gtaagttgga caattcaatt caattatctt      240
cgtagcgggt tttcttgtgt ttcaaactgg ctaggtggtg gttcttgtaa aaagctagct      300
t                                                                      301

<210> SEQ ID NO 109
<211> LENGTH: 301
<212> TYPE: DNA
<213> ORGANISM: Glycine max
```

```
<220> FEATURE:
<221> NAME/KEY: unsure
<222> LOCATION: (1)..(301)
<223> OTHER INFORMATION: unsure at all n locations

<400> SEQUENCE: 109
gtattattag canaatgcct ctatgcaaaa cctttggtct tatgaattgt gttatgtttc      60
acttcaacga acaagaaaaa cactcattat tctccagacc agtaaaagta acaatggtct     120
caattctcaa actcagcaag aaacgcttca aacgtcctag aaagcaagcc attatgacca    180
tcataatcaa accaaaaagg ttacaagtgt atcagctttt gaacagagtc cactcggctc    240
aaagtgaaga aattttaaac acttacacgt cctctgcact tttttcgact tttnaatcca    300
a                                                                   301

<210> SEQ ID NO 110
<211> LENGTH: 301
<212> TYPE: DNA
<213> ORGANISM: Glycine max

<400> SEQUENCE: 110
gaagaaaact tacaaagtga aaatatatt tcaaaaagtt attatttcta cattattaga      60
gttatttatt tagaggccat tcgaatgaga tgttttgcaa acaagcgttg gagaaaatag   120
agtcgactat gtatttgagc aaaaaactat aagcagtact ttcttttacc aaatgctcat   180
agcaaaagga aactgtgggg aaatgattct tggggttagt ggttacaaaa ataagtaaat   240
aactgccctg gtgcagttgt aaatctaaca agagatatct ctaaatgaag agtttcatta   300
t                                                                   301

<210> SEQ ID NO 111
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 111
aaaataaatc ctatgaataa taacttattt gctgttgctt ttgtaatgtt ataaaagctt      60
ttttctttcg dacgcttttt ttatttgccc tttttgcaca gcacttgcca atttatggaa   120
tagcccgtga gatctgtaat tttctgtatc ccttccccac attggagaac taggctaatt   180
tatatccatc tcttagactt tgtacgaaat cgaaatgcaa ataaataatg agaaatcata   240
gatgcagagc ctactaantg tatatattag taattattac tatagtgcca acaaaagcaa   300
a                                                                   301

<210> SEQ ID NO 112
<211> LENGTH: 301
<212> TYPE: DNA
<213> ORGANISM: Glycine max

<400> SEQUENCE: 112
attatttgta agggctggat cctttgaata attactccta taaagactgg gctgatctta      60
tataagaaat atgttaaatt ataaatttct acaagtatta ctgcaatttt atgagaattt   120 gttttttctat tgtaaattgc aatatatttcc cccggatccg gaatagcctc atattgactc   180
caaatagtca tgacaaatga agattgaggc gggatttggc attttttaaac cactgctagt   240
```

```
gcttggtttc cattttggtt gcaagtgtaa ccaaccagct attaaagata caattggaag    300
a                                                                   301

<210> SEQ ID NO 113
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 113
tctcctcgat gagatccagc ttctcccttt cctccacggt ctgaggcagt ctccctactg    60
agaagtgcag aggttgcagt gggcggtgtt gatgagctcc catggcattg ggctgaggca   120
taccatcaaa tgtcggtccc tcancggtga atgtggagta tagttcaaag tcacccacaa   180
catgatctcg agggtcttca tagggttccc ccataggctg agggatgggt gtacgtccca   240
antggggttg ctggccctca aanggaatgg gaanggagtg gttggcgttc tcggtgggca   300
t                                                                   301

<210> SEQ ID NO 114
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 114
ctcctcgagg ccaccatcat tnggatcaaa atattccggt ctacctatcc tagaagttat    60
tgtcctggcc tcccatccac gtgcgtgttt tttcaagcnc caaacaacac cttgtgttgg   120
tgcttcttgg cagngcatcc gaccnncttt tcggctgccn tttctagcga cagactcacc   180
ggaccgaggc gcacaaagtg tctcaccttm ttttgggcca ttctgagatt cttcccttg    240
ccgtaccttm ttttagttca cgttgtttgg tcattgtttt gcccttgttt tcaagttcga   300
c                                                                   301

<210> SEQ ID NO 115
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 115
tgctatggta gatcagtaag gaaccaagta ntattnacct ctaatgcttt aatctttgca    60
ttcatagctt caatccagtt aggatcttta gaggcnacan tgtatgattg aggttcaact   120
tgttgtgtaa caaacaagat aacctttga taggaagtag atagtctgtt ataagaaaga   180
acagaacaga gaggataaag agtagtacct gtagagagat tggcaacaat tgatgatgga   240
tatgtgatgt gaaagtcttt tatacttgct tggcctttgt ctctgtctca ttggccttct   300
a                                                                   301

<210> SEQ ID NO 116
<211> LENGTH: 301
```

```
<212> TYPE: DNA
<213> ORGANISM: Glycine max

<400> SEQUENCE: 116
acttgtaact aactaagcta actctagtta caatgtgatc aatctgaatt aaccattatc    60
aaaacagtat ctatgctaag acatagcttg ccttaattgt gacctctttg gaggttgcct   120
taattgcagc agcctagagg gggtgtgttt aggccacatt gcctacaaat atggcctaga   180
tagtgcttac aaggcttggg taatcctcac attacaatgc ggtgttttgg agctgagata   240
ggttctaagc tcaaattcta agagattttg gtggcctgaa gactgaacaa cattttctgc   300
t                                                                   301

<210> SEQ ID NO 117
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 117
ttatttgttt cttccttttg ctgctgactt ataattgaag gagtttctgc tgtgtttgtg    60
tcatcccgcg aaaagagagc ctcacatttc tgggctaatt tcttttgcc cccnccttt    120 cgggaataca ccagccagga gttatttggg catggtgtgt ggccttttgg gcttgctttt   180
tggggagcaa atgttttggg aggggtgtaa atatcacagc ccaagtccac taggctttcc   240
acctccttgt cacgtgcctt ttgtctccca tatttaaaac tgccgagctc ttcaacgttc   300
a                                                                   301

<210> SEQ ID NO 118
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 118
aaaaantaaa ttctaaaatg gttttttgaa aaatcgtctt agaatgcata tcctttaag    60 atggttttta caacgaacc gtcttagaaa agtatcattg taagacagtt tttaccaaag   120
aaccgtctta gaatgatatc tttttttcta agacggttac ttaaaaacta tcgtaaaaag   180
taaagacttt ttataatgtt atctacgacg aaggttaata atcgtcgtca aaggtctctt   240
ttaaccgaca taaaaagcgc tttgtgtaac agtgcatatc cataatttat acccgtttat   300
a                                                                   301

<210> SEQ ID NO 119
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 119
gtcccttgtc attgcctaat aaattaaggt ggcttcattg ggatcaatgc tttcttaagt    60
```

```
cttttctaac taacttttgt gttgaacaac ttgtagttct ttggatgant ggttgcaagc      120
ttaaaaagct ttgggatggg gttcaggtat gcatgttgct atacataata caattttctt      180 tcaattttt atggcatggg tacaagagag agtcctaagc ggtaattggt ttcatgttgc       240
ctcaagtgaa gctcattcct aagagcaagg gctacactta ggatgttttg cttctattta     300
t                                                                      301

<210> SEQ ID NO 120
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 120
ataaatgaaa aaactaatt attattgtat taaaaaatta aataataat tatctttaga        60 taagtttttt nttctcacac aacaattatt ataggacaaa gactgtactt gtagggttat     120
gcaaacgagt ctgacttcct agtttaaaaa atgaggttgg ccttggaacc tctgaggtta     180
gaagcctccc caagtctcga agtgcatgac aaatcaagga gtggccttga atgtataccc     240
ttactaggca ttgttaaacc ctagggaagc gtgataaagg ggaagggaaa tggttaggag     300
a                                                                      301

<210> SEQ ID NO 121
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 121
gaganaggct agcgcttgtc tggcttgtgc ctcttgtccg gcttgtgcaa gtcagccttg       60
gngtttattt tgcacttgtc acgcttctat ctggcttagt ggacttcatt ctgtaatctn    120
gacaatgctt ccatgtggat gtagcccttg gctcactcgt gcagctagtc catgcaattg    180
agtggtcttt tgcacaaact atctgtgaac ttgtcgagga ataatgtgag gagcattgaa    240
tggaacacta cctcggggta agatttcgga tctggacggt tgtgcgccca aatctgccca    300
t                                                                      301

<210> SEQ ID NO 122
<211> LENGTH: 301
<212> TYPE: DNA
<213> ORGANISM: Glycine max

<400> SEQUENCE: 122
caataaatat aagattgact taattaatga taaagaaaaa aaaagaaaa aagttatgaa        60 tttaaattct ccacaaataa aaattaataa ttaacttta tggatctaaa aaaaattacc     120
tcatagactg tgccatcacc caactgaaca agggtaaaaa gctttctgtc tgtagtgctt    180
gcagccacag aaagtaacca tggagcataa acagacattg tagaaagctc tggaccctca    240
ttaccagcag aatgggacgt taatattcct ttcttcattg catggaaagc cccaatggcg    300
a                                                                      301
```

```
<210> SEQ ID NO 123
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 123
ggggtatgcg aggctacnga gaggggaagt agggaaaaat gatgaaggct aggatgtgga      60
cggctccgga gacctttgcg gtgctctagg agtttctcct cctgaagatg ggccaagtcg     120
gtggcatgca ccagcgtcaa cggctanaga gcttggaatt cangccggat gtccgattcg     180
aggcctgaga tgaagcaacn tagaagtgat gatggtgaca acccaacaat gcgattggcg     240
agtgcttcaa attgagccag gtattctctc antgaatctt tctgggttaa tttaaagagg     300
a                                                                     301

<210> SEQ ID NO 124
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 124
aggtatcgtg gcctgttgat tctccttttt gtcccttgtt cttcttcttc atttggttct      60
aatattgatt ctgagttttg ctttgtaatt gttgactctg ttttcataac acctaattaa     120
attaaatata ctcttatgcg acttttggtg tacaaaattc atcatgagct ccttcgtcat     180
ttcaagggct cttcgaaagc tnacaagcgt cttattctca ttggtatcta tctccatctc     240
tctctttctc tctctctctc tctctcaata tatatattaa ataaaagaa aaattgccat      300 a                                                                     301

<210> SEQ ID NO 125
<211> LENGTH: 477
<212> TYPE: DNA
<213> ORGANISM: Glycine max
<220> FEATURE:
<221> NAME/KEY: unsure
<222> LOCATION: (1)..(477)
<223> OTHER INFORMATION: unsure at all n locations

<400> SEQUENCE: 125
accttgcaac atataagaca gatagcacaa gaatcaagtg gagaaattca gtatggtggc      60
ggacaccaac ttgctgtttt aagaacattt agccacagac tttgcaggta attaaggcag     120
actttaatgt ccttggtagt tcgaaccaat gcattgtgca ttttagttat tgacttggca     180
ttttaaactt gatgtaatta agtagtagtt tgttcattaa ttattctnat tcttgctaaa     240
attcaagctt gtncattacc attgcttcat aattactatg ttttattgaa attgcattcc     300 ttagggggctt taatgatgtt gtgaatgggt ttgttgatga tggctggtca ctgatggggt    360
ggaagatgta actatagcca aaaactcatc tccaaacaaa ttttgggat ccaattacaa     420 tgcatcaatg tttccagcat ttggggggtgg ggtcttgtgt gtcaaggcat caatgct      477

<210> SEQ ID NO 126
<211> LENGTH: 301
<212> TYPE: DNA
```

<213> ORGANISM: Glycine max

<400> SEQUENCE: 126

```
ttttacttaa catggtatct agagtctaac tgagggaata atgaaaatca tgccccacca    60
agaacctaca agatagtagg tccccgatgg atctttctac tcatctccct tcttttggca   120
acttgtttct gcattccgat ggacccttt tgctcgttgt tgaacaacaa ccttttcatg   180
cttttctggc caccatcgtt tgtcattatt gaaacttcag caacctatcc agactctaac   240
catcaaatct ggtgcacctt tggccgacct gtctagattc aaccaccgca agtcaattgg   300
a                                                                   301
```

<210> SEQ ID NO 127
<211> LENGTH: 902
<212> TYPE: DNA
<213> ORGANISM: Glycine max

<400> SEQUENCE: 127

```
atggacaagt ttaatctcac cttttacaat ggtttgtgat gacattagga aagacctaca    60
gtaacatgtc ctgtatttac tgtgtattat tttaaattct tgatatccgg ccctcatatt   120
agaagggatc cttacggaag aaagttttta tgtggtcttg ctcgtaggcc aagtaaacgc   180
aaaaacgtat gaaagatcaa gaaaggaaat ccagaaaata tgtcatttga taaacctaat   240
tgaacccatt ttctatattt tcctttcctg cccaaatatt tatgtataag cttccttcaa   300
cttgtctaca tctctgtcac tttatgactg cccttttatag catctccaat aatgaacatc   360
atttagtttt tttaactctt ttaatggctc ttaccatccc acatcggttt taagaacttt   420
agcaacttt cactccaatg atgcatctct gtaagaactt aaacaggtct caagtttttt   480
acatcttaat ttttctttaa tgggtctcag acgttacctt tcaattgttt tttaatggtt   540
aagagtcagt tcttttataa gaacagttct tactcgtaat gtccatatca tcttcctcca   600
gtggtgaacc tagttaaaaa tggttcttaa ctttaagaac ctacacaaga actatcttag   660
agatgctctt gtagtgaagg tataggttgt tctaagatgg tcacatcaat cacagatcac   720
cttatgtgtt ctatatttag aatttaccttt gtctgttaca tcttaaagac gatactgaat   780
tactgatgct tatgcagttt gaggatgatg tgtacttgcc aacggatgag ccacatgggt   840
caattcaagc tagtatgagc cgcttgtgtc aaagctgtag aaactgcagg catacaaggt   900
tg                                                                  902
```

<210> SEQ ID NO 128
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 128

```
tagtatgact aagattaaaa aaaaaaagaa gtcagtggaa gattttttcaa attgaaataa    60
aaaaaatacg aatcttctac tccttaaaga atttgggaaa aggggtagag tgattataca   120
tgcatttgaa ataaaaaaac acacacgcca aagagcccgt taatattggc cacagggtgg   180
tgttgacgag ttataactat atgccttgaa ggaaagaagt ttttttttn aaaaaaaaa   240
aaaaaaagc caaatggtat tataaacaac aaacaaagca caagtagtgc ctaatacaag   300
a                                                                   301
```

<210> SEQ ID NO 129
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 129

```
aacacaacat gaactattta tacttcacat ttgctcacgc atttcatcaa ataagttgta      60
ggcaagttgg ttaaatactt aaatcccaaa agtcctaaca accagcccaa cacaaggcat     120
caactaccat tcaacatcat gtaggacaag tgaacaaagc acagtagatt aggtgggaga     180
aggacatacc tacggacacg acagagcgtg acaaataacc accaggacat gatgatgagt     240
gtgcattttc agtttgcgag gtggaccttg cgncggagag tgttttggca ggctggagaa     300
g                                                                    301
```

<210> SEQ ID NO 130
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 130

```
aattgatgct tctaagttct aatcgcactt caacacngaa atttaggagt gacgagaaat      60
agagccctac tttctttctt gccgcgtttt atataataat ttggggttgtg aaagttgggc    120
ttggacngng gaacacagat gncccacaac aaatgggccc taatggagaa agaaaatgtg    180
gcccaggtca ctttaaaaaa aggaaaagga aaggaatac tgccaatcaa aataaaataa      240
aataaagtan attgatanca tgggctaaca tgtcttgccc cattacaagt ccttttttt     300
t                                                                    301
```

<210> SEQ ID NO 131
<211> LENGTH: 301
<212> TYPE: DNA
<213> ORGANISM: Glycine max

<400> SEQUENCE: 131

```
taatgctctt aggcgtattt ttcgtttatg ctacttttat aacatcgaac attttttattt    60
tctttagga gaaagaaaga aataaggtcg ggatatgcct ttggctgtct gtttgtaagc     120
atgcatgcat acatccggcc ggtgctggag aatatttgct tatcaccatg gcacaaacgc    180
attattcatt attttcccct ttttaccaac ttaaaacagt ttcttatatt atcgagtttc    240
atagatataa tcatttcagt taagcttaaa aaattggaga atctctataa tttaaattga    300
t                                                                    301
```

<210> SEQ ID NO 132
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 132

```
tttcttaaat ctaacaatgt tgncttaatc tccaagatgg tttggaccat catggtctct      60
attaatctcc acatgacacc taattaagta ttattaattt tttcttgtaa attaacaaaa     120
tngagtacat gtcaattaag attattcaag gcaatagaca ggtagtggtt ccaaactact     180
tatctatatc ctaagacaac anaaatctan attgagcata taccttgtcc tcgataaggg     240
gagagtcatc agcaaaccat gtctcctgtc tctcagactg acaatgagca aaacaagaat     300
t                                                                    301
```

<210> SEQ ID NO 133
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 133

```
aatgatggtt ccttatttat atattttatt taatataag attattttta atgaaaatgt      60
acaacttaaa ttatttccaa caacatgtta taaggaatta tcttgaaaaa tgaatctaag    120
gtttcaatct cattggatag agtctcacaa gtttcttttc aatacactct acatgaaggc    180
aactcgtgcg gattggcttg acaagcatgg atcatctcat gatgaagctt tttaatttga    240
atacttatc cacagattat tttagccgat gctntgggga ttatgaggat tcgcgtttag     300
t                                                                    301
```

<210> SEQ ID NO 134
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 134

```
actttgcaat gaganaaaaa cgaaccttgt atctgtcagg gatgaagctc aaaaagtcac      60
tctcaagact gtgcaaacac atcaattcga atgagttatg taattaatga tatattgtgg    120
atcatacaaa aaaatgaat acaagtatag ttcactcgtc actgctcatt ttgtaaatct     180
tcatgcttgg gctatacgc cctctagaat atcttcaagg tctggaccac cctgatcttt     240
acgttgaagg ttgaaccaat atgccatttt agactttaga gttaagagag agtttacaat    300
g                                                                    301
```

<210> SEQ ID NO 135
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 135

```
tttctgtatt ttctaaatcc aatcccacct ccaacgaaat gtctatagta ttaggcactg      60
catattgaga gatatgtatt gaatgttggc naaaaaaaaa tgcactcaaa ctttaaattt    120
attaaacgat atagcacang ctttgtcaaa ttctatcagt tttccagcac acagtggtgt    180
```

```
tatatctgta aattgggtgg atattatgtt ttctatgtag gtggtatttt agacgtggat    240
gtatggtttg gagaaatatc aagggaggaa atttactata agtgtgctgg aaaactgata    300
g                                                                    301

<210> SEQ ID NO 136
<211> LENGTH: 301
<212> TYPE: DNA
<213> ORGANISM: Glycine max

<400> SEQUENCE: 136
cgtgcttctg aaaaagcctt ttttgaacac cttttcctag ttatggaaac gctattccaa    60
aagcattttt ggttatggga tggtccttcc ggaagttgtt taacatataa ttagatttga    120
ttttgttatt ttacagtttt agtaattttt tattttatag atttattctt gatttgtatg    180
gaggatgatt acttcaacaa tatgtcagat gaagttggca tggatatgaa tgtgttaact    240
gattgacaag tgtaccaaaa gtctaaataa taaagactcg aaagttcgag tgtcgatttc    300
c                                                                    301

<210> SEQ ID NO 137
<211> LENGTH: 301
<212> TYPE: DNA
<213> ORGANISM: Glycine max

<400> SEQUENCE: 137
taaccattat tgcattgcca tactgttcag cttctcgtag gatatcttct tttaatcgag    60
cctccatttt ctctaccctt tcacgaccaa ttccctgaaa gcacaaattg caatatccaa    120
ttcagagaat ttggcacaaa attgacaaac tgctgtgaaa ttatgaggca ccaaatggca    180
tcttagattc tacttagata agcttcatgc tatatctact tcagcattag catgaatgtg    240
tatatttttt gaaatttccc ctaacctgca gcaaacaaag tgaaggggat ttggccagat    300
t                                                                    301

<210> SEQ ID NO 138
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 138
gccatcgcct ctagcgttgc agttttttgt tttattttc cctcgccaca cccanaaaag     60
gcaaatgagt tgcaatctnt gggaggaaac ctgacccata ncgaattgaa gaaaagctca    120
aagtggcaat gtnaagggtc cattnttgtc atcatctctt agtcgaaggc cactatagaa    180
gtaggaagga agtgttcacc aatctttgtg ctccccgaca aacctgtaat ttgccgatga    240
gttttcgacn acaataattg cactcgaaca cttaccctag ccattttagt ttatcatagc    300
t                                                                    301

<210> SEQ ID NO 139
<211> LENGTH: 301
<212> TYPE: DNA
<213> ORGANISM: Glycine max
<220> FEATURE:
<221> NAME/KEY: unsure
<222> LOCATION: (1)..(301)
```

<223> OTHER INFORMATION: unsure at all n locations

<400> SEQUENCE: 139

```
caaacttttta tgtgatatcg aaacgactat tgggcttcaa ttaagtagaa acaaagggcc    60
tacataggat tattagttta ttaaaacatg tgatgtcacg gtgggccaca ngaagcagta   120
acaaaagacc ctcacagtat gggctaatat ttcacgcatt gccgacgtaa cgaggtgtca   180
ccttttttcac cgtcttcaac atttagccgg gtcactttaa cccgattaca gcccacaaac   240
ctgaatagaa acctaatgat ttctctagcc aacacggaac tcatcgttta aatttnnaga   300
a                                                                   301
```

<210> SEQ ID NO 140
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 140

```
atggatgggg tggcaatggc ggaaggaacg gaagagagtg tggcgtcacg gttacgggga    60
agggngttga agaaaacgga ggtggttgtg gcggctggtc ttttgaagag ttgaaaagag   120
ggggtttttgt atatggagat ggaagaagag ataccctatgg ttgaagccat ttggagggag   180
gaaatgaaag aagaagaaga agaggaggag gcggcgaggg gataaggcca cgcacctttc   240
tgtctctgaa cttaaagcct tttaaacctc cctgtgctgc gtgcgtatca ctgtgtgtct   300
g                                                                   301
```

<210> SEQ ID NO 141
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 141

```
taatctctcc caagtccnga ccaaaccaan caatcctctt gataatnggt cttcagtctt    60
gatactgtaa ttgtctccac tgattgtgaa tcgtgtgcac atcgtagata cagaaatggt   120
tgacttactt caaacacgac gacaggtcct gagtgtatnt ggattttaac taaattaact   180
aattgatngg ttatttttctc tttcgcacct tgaataccta tcaccgttcg atttcataga   240
atgccattgc caccattttt tttttatctt ttttaaattt gctctacnga tttttnctcc   300
a                                                                   301
```

<210> SEQ ID NO 142
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 142

```
ttgattataa gatattatat aaattaccaa aatttctatc attaatttga caaagtacta    60
ataacgggtc agaagtgata aggatttata tctcttaatc aagtnntata aggtttgatt   120
```

```
cctgcacgtt gatnttttgaa tatagaataa atcatgttgg accagagaag aatactcatc    180
ttgtgtgtca tcattccgac caagattaat caccacttcc aacaaaacta cttcatacta    240
atattatcat tagaaaaaaa antaacttaa tgaattttta tgaacaggaa tatagctaca    300
t                                                                    301

<210> SEQ ID NO 143
<211> LENGTH: 301
<212> TYPE: DNA
<213> ORGANISM: Glycine max

<400> SEQUENCE: 143
ggggcttgac aaactcatca ccccctact tgtcaaggct actacccga atatcagaca      60 atcttcaaca ctggataacc tctttcacct tcaatctagc tcagagcttg ggggcttat    120 gtactgtcca gggtccgcaa atacatgta gcatcctaca tggcactctg aaacttgtgt    180
catccctcca tgtcaaccca agaacaggag cactaacatt cgatccttat tagctaggct    240
cccccaacca acaggttatc cctaacctct taatatttga atatattgtt accattttat    300
c                                                                    301

<210> SEQ ID NO 144
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 144
gctgaggtcg aaaaatccga cgattctctg gcgttagagg cttctgctga agatagtgtg    60
aaacatgaca gggntgagga agcacaaagt gcaacaccac ccccaacaga aggagatgat    120
cacaaggttg agcctgctgt tgcagtagaa aagattgaag attctgtgcc atcagatgaa    180
tctgtcgttg cagttgaaga tagtgtaaag gaggagaagg aagtggttcc tgactcacac    240
actatcagtg acattgaacc agttcatcag gcnccatcca cagaacaagc tgtggagaaa    300
a                                                                    301

<210> SEQ ID NO 145
<211> LENGTH: 301
<212> TYPE: DNA
<213> ORGANISM: Glycine max

<400> SEQUENCE: 145
gtttcacttc tttgagtttt ggatttgttg ttattattat aaggaaaggg tttagaataa     60
tcatttgaaa ttataagaaa ggatttaatt gattaaagac aagtgcttta atcaattgtc    120
atcaggtaga atctaagaaa ttgctaagcc tttagttcgt tttaatacat gtggtcccct    180
tatttaaatg tcacttggat atccctcgtg ccctttgttt taagcaaaga taacattatg    240
gtacggaggt cattgtcgcc atttttccaag gatgcatttt aatttagttt agataacttg    300
a                                                                    301

<210> SEQ ID NO 146
<211> LENGTH: 301
<212> TYPE: DNA
<213> ORGANISM: Glycine max
```

```
<400> SEQUENCE: 146
tccagagctc aacttgttat taggacgtga gataggaaga cttatcagta cgtgagatag        60
ataaaagatg aatgcgtgat ttgttactga aggtgattgc aaatatattt gcaaagatat       120
gggttgaatg tagataaaaa atgaatcaga ttcagaaata actaaatttt ccaaaataat       180
aaaatataaa aagaacgtcg agaatgcaac gtggcttcca acatacatgt tagaacattg       240
ttcttgtgac ttcgaaatat cacctcctta aaaatttagt ctcactcaag gaccaacctc       300
a                                                                      301

<210> SEQ ID NO 147
<211> LENGTH: 301
<212> TYPE: DNA
<213> ORGANISM: Glycine max

<400> SEQUENCE: 147
ctgattagtg tgcgtgtgta gcagctaggt gtcgaatata taaccattgt aatgcattgg        60
aaaatcagaa aatgaaggaa ttcagtttaa atatctattt cttctctctt cctaatcttt       120
atcgagttct ctcttactgg aaaaaggtct tgtattactt tgttttcgtg aaaagtttaa       180
tatcggattt gttggacatg tatacatttt ctatttttct tgtgattttc ataataataa       240
aaaaaaaatt ataattttga ttttaatttt caaattcatg attttaaaac atttgatttc       300
c                                                                      301
```

MOLECULAR MARKERS ASSOCIATED WITH SOYBEAN TOLERANCE TO LOW IRON GROWTH CONDITIONS

CROSS REFERENCE TO RELATED APPLICATION

This application is a continuation of U.S. patent application Ser. No. 14/300,384, filed on Jun. 10, 2014, which claims the benefit of priority to U.S. Provisional Application Ser. No. 61/833,129 filed Jun. 10, 2013, which are each hereby incorporated by reference in their entireties.

INCORPORATION OF SEQUENCE LISTING

A sequence listing containing the file named "Seq.P34215US02.TXT" which is 99,955 bytes (measured in MS-Windows®) and created on Jul. 12, 2018, comprises "147" nucleotide sequences, is provided herewith via the USPTO's EFS system and is herein incorporated by reference in its entirety.

BACKGROUND OF INVENTION

Soybean, *Glycine max* (L.) Merril, is a major economic crop worldwide and is a primary source of vegetable oil and protein (Sinclair and Backman, Compendium of Soybean Diseases, 3rd Ed. APS Press, St. Paul, Minn., p. 106. (1989). Growing demand for low cholesterol and high fiber diets has increased soybean's importance as a health food.

Soybean varieties grown in the United States have a narrow genetic base. Six introductions, 'Mandarin,' 'Manchu,' 'Mandarin' (Ottawa), 'Richland,' 'AK' (Harrow), and 'Mukden,' contributed nearly 70% of the germplasm represented in 136 cultivar releases. To date, modern day cultivars can be traced back from these six soybean strains from China. In a study conducted by Cox et al., Crop Sci. 25:529-532 (1988), the soybean germplasm is comprised of 90% adapted materials, 9% un-adapted, and only 1% from exotic species. The genetic base of cultivated soybean could be widened through exotic species. In addition, exotic species may possess such key traits as disease, stress, and insect resistance.

The availability of a specific micronutrient, such as iron (Fe), is often related to soil characteristics. Soil pH has a major impact on the availability of Fe. Iron deficiency has been a common, serious, and yield-limiting problem for soybean production in some parts of the United States.

Iron is one of the necessary micronutrients for soybean plant growth and development. It is also needed for the development of chlorophyll. Iron is involved in energy transfer, plant respiration, and plant metabolism. It is also a constituent of certain enzymes and proteins in plants. Iron is necessary for soybean root nodule formation and plays a role in N-fixation; thus, low levels of Fe can lead to reduced nitrogen content and poor yield.

When iron is limited, soybean plants can develop iron deficiency chlorosis (IDC). Soybean IDC is the result of a complex interaction among many factors including soil chemistry, environmental conditions, and soybean physiology and genetics. The most common IDC symptom is interveinal chlorosis in which leaf tissue of newly developed soybean leaves turn yellow, while the veins remain green. The leaves may develop necrotic spots that eventually coalesce and fall off the plant. Iron deficiency symptoms are similar to that of Manganese (Mn) deficiency; therefore, only soil and tissue analysis can distinguish the two micronutrient deficiencies.

Severe yield reductions due to IDC have been reported throughout the North-Central U.S. with losses estimated to be around $120 million annually. In some instances, yield loss can be greater than 50%. Typically, soybean IDC symptoms occur between the first and third trifoliate stage, so under less-severe iron deficiency conditions, symptoms may improve later in the season.

Soybean plants grown in calcareous soils with a pH of greater than 7.4 or in heavy, poorly drained, and compacted soils may exhibit IDC symptoms due to insufficient iron uptake. However, soil pH is not a good indicator and does not correlate very well with IDC. Symptoms are highly variable between years and varieties and depend on other soil factors and weather conditions.

There is, however, a direct relationship between IDC incidence and concentrations of calcium carbonate and soluble salts. Iron uptake is adversely impacted by high concentrations of phosphorous (P), manganese (Mn), and zinc (Zn). Moreover, high levels of calcium (Ca) in the soil cause Fe molecules to bind tightly to the soil particles, making them unavailable for uptake. Therefore it is important to monitor the levels of calcium carbonate and soluble salts in the soil. Sandy soils with low organic matter may also lead to a greater incidence of IDC symptoms.

Weather also plays a role in IDC symptoms. Cool soil temperature and wet weather, combined with marginal levels of available Fe in the soil can increase IDC symptoms.

Soybean producers have sought to develop plants tolerant to low iron growth conditions (thus not exhibiting IDC) as a cost-effective alternative or supplement to standard foliar, soil and/or seed treatments (e.g., Hintz et al. (1987) "Population development for the selection of high-yielding soybean cultivars with resistance to iron deficiency chlorosis," Crop Sci. 28:369-370). Studies also suggest that cultivar selection is more reliable and universally applicable than foliar sprays or iron seed treatment methods, though environmental and cultivar selection methods can also be used effectively in combination (Goos and Johnson (2000) "A Comparison of Three Methods for Reducing Iron-Deficiency Chlorosis in Soybean" Agronomy Journal 92:1135-1139; and Goos and Johnson "Seed Treatment, Seeding Rate, and Cultivar Effects on Iron Deficiency Chlorosis of Soybean" Journal of Plant Nutrition 24 (8) 1255-1268).

Soybean cultivar improvement for IDC tolerance can be performed using classical breeding methods, or, more preferably, using marker assisted selection (MAS). Genetic markers for low iron growth condition tolerance/susceptibility have been identified (e.g., Lin et al. (2000) "Molecular characterization of iron deficiency chlorosis in soybean" Journal of Plant Nutrition 23:1929-1939). Recent work suggests that marker assisted selection is particularly beneficial when selecting plants because the strength of environmental effects on chlorosis expression impedes progress in improving tolerance. See also, Charlson et al., "Associating SSR Markers with Soybean Resistance to Iron Chlorosis," Journal of Plant Nutrition, vol. 26, nos. 10 & 11; 2267-2276 (2003). U.S. Pat. Nos. 7,977,533 and 7,582,806 disclose genetic loci associated with iron deficiency tolerance in soybean.

There is a need in the art of plant breeding to identify additional markers linked to genomic regions associated with tolerance to low iron growth conditions (e.g., IDC tolerance) in soybean. There is, in particular, a need for numerous markers that are closely associated with low iron growth condition tolerance in soybean that permit introgression of such regions in the absence of extraneous linked DNA from the source germplasm containing the regions. Additionally, there is a need for rapid, cost-efficient methods to assay the absence or presence of IDC tolerance loci in soybean.

SUMMARY OF INVENTION

The present invention provides for methods of creating a population of soybean plants with a low iron growth condition tolerant phenotype, comprising a.) providing a first population of soybean plants; b.) detecting in said soybean plant an allele in at least one polymorphic nucleic acid marker locus associated with the low iron growth condition tolerant phenotype wherein the marker locus genetically linked by less than 20 cM to a linkage group J genomic region flanked by loci ASMBL_10470 and TC370075, linkage group E genomic region flanked by loci DB975811 and GLYMA15G06010, linkage group M genomic region flanked by loci TA75172_3847 and TC380682, linkage group D2 genomic region flanked by loci TC350035 and Gm_W82_CR17.G8870, or linkage group O genomic region flanked by loci NA and Cf16144d; c.) selecting said plant containing said allele to provide a plant having a genotype associated with a low iron growth condition tolerant phenotype; and d.) producing a population of offspring from at least on of said selected soybean plants.

In some embodiments of the invention, the marker locus is genetically linked by less than 15 cM to the linkage group J genomic region flanked by loci ASMBL_10470 and TC370075, linkage group E genomic region flanked by loci DB975811 and GLYMA15G06010, linkage group M genomic region flanked by loci TA75172_3847 and TC380682, linkage group D2 genomic region flanked by loci TC350035 and Gm_W82_CR17.G8870, or linkage group O genomic region flanked by loci NA and Cf16144d.

In some embodiments of the invention, the marker locus is genetically linked by less than 10 cM to the linkage group J genomic region flanked by loci ASMBL_10470 and TC370075, linkage group E genomic region flanked by loci DB975811 and GLYMA15G06010, linkage group M genomic region flanked by loci TA75172_3847 and TC380682, linkage group D2 genomic region flanked by loci TC350035 and Gm_W82_CR17.G8870, or linkage group O genomic region flanked by loci NA and Cf16144d.

In some embodiments of the invention a second marker locus associated with the low iron growth condition tolerant phenotype is in linkage group J genomic region flanked by loci ASMBL_10470 and TC370075.

In some embodiments of the invention a second marker locus associated with the low iron growth condition tolerant phenotype is in linkage group E genomic region flanked by loci DB975811 and GLYMA15G06010.

In some embodiments of the invention a second marker locus associated with the low iron growth condition tolerant phenotype is in linkage group M genomic region flanked by loci TA75172_3847 and TC380682.

In some embodiments of the invention a second marker locus associated with the low iron growth condition tolerant phenotype is in linkage group D2 genomic region flanked by loci TC350035 and Gm_W82_CR17.G8870.

In some embodiments of the invention a second marker locus associated with the low iron growth condition tolerant phenotype is in linkage group O genomic region flanked by loci NA and Cf16144d.

Also provided herein are methods for creating a population of soybean plants comprising at least one allele associated with the low iron growth phenotype comprising at least one of SEQ ID NOs: 1-147. In certain embodiments, these methods comprise a.) genotyping a first population of soybean plants, said population containing at least one allele associated with the low iron growth condition tolerant phenotype, the at least one allele associated with the low iron growth condition tolerant phenotype comprising at least one of SEQ ID NOS 1-147; b.) selecting from said first population one or more identified soybean plants containing said at least one allele associated with the low iron growth condition tolerant phenotype comprising at least one of SEQ ID NOS 1-147; and c.) producing from said selected soybean plants a second population, thereby creating a population of soybean plants comprising at least one allele associated with the low iron growth condition tolerant phenotype comprising at least one of SEQ ID NOS 1-147.

Further areas of applicability will become apparent from the description provided herein. It should be understood that the description and specific examples are intended for purposes of illustration only and are not intended to limit the scope of the present disclosure.

DESCRIPTION OF INVENTION

I. Definitions

Unless otherwise indicated herein, nucleic acid sequences are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains.

As used herein, an "allele" refers to one of two or more alternative forms of a genomic sequence at a given locus on a chromosome. When all the alleles present at a given locus on a chromosome are the same, that plant is homozygous at that locus. If the alleles present at a given locus on a chromosome differ, that plant is heterozygous at that locus.

As used herein, the term "bulk" refers to a method of managing a segregating population during inbreeding that involves growing the population in a bulk plot, harvesting the self-pollinated seed of plants in bulk, and using a sample of the bulk to plant the next generation.

As used herein, the term "comprising" means "including but not limited to".

As used herein, the term "locus" refers to a position on a genomic sequence that is usually found by a point of reference; e.g., a short DNA sequence that is a gene, or part of a gene or intergenic region. A locus may refer to a nucleotide position at a reference point on a chromosome, such as a position from the end of the chromosome.

As used herein, "linkage group J" corresponds to the soybean linkage group J described in Choi, et al., Genetics. 2007 May; 176(1): 685-696. Linkage group J, as used herein, also corresponds to soybean chromosome 16 (as described on the World Wide Web at soybase.org/LG2Xsome.php).

As used herein, "linkage group E" corresponds to the soybean linkage group E described in Choi, et al., Genetics. 2007 May; 176(1): 685-696. Linkage group E, as used herein, also corresponds to soybean chromosome 15 (as described on the World Wide Web at soybase.org/LG2Xsome.php).

As used herein, "linkage group M" corresponds to the soybean linkage group M described in Choi, et al., Genetics. 2007 May; 176(1): 685-696. Linkage group M, as used herein, also corresponds to soybean chromosome 7 (as described on the World Wide Web at soybase.org/LG2Xsome.php).

As used herein, "linkage group D2" corresponds to the soybean linkage group D2 described in Choi, et al., Genetics. 2007 May; 176(1): 685-696. Linkage group D2, as used herein, also corresponds to soybean chromosome 17 (as described on the World Wide Web at soybase.org/LG2Xsome.php).

As used herein, "linkage group O" corresponds to the soybean linkage group O described in Choi, et al., Genetics. 2007 May; 176(1): 685-696. Linkage group O, as used herein, also corresponds to soybean chromosome 10 (as described on the World Wide Web at soybase.org/LG2Xsome.php).

As used herein, "polymorphism" means the presence of one or more variations of a nucleic acid sequence at one or more loci in a population of at least two members. The variation can comprise, but is not limited to, one or more nucleotide base substitutions, the insertion of one or more nucleotides, a nucleotide sequence inversion, and/or the deletion of one or more nucleotides.

As used herein, "genotype" means the genetic component of the phenotype and it can be indirectly characterized using markers or directly characterized by nucleic acid sequencing.

As used herein, the term "introgressed," when used in reference to a genetic locus, refers to a genetic locus that has been introduced into a new genetic background. Introgression of a genetic locus can thus be achieved through both plant breeding methods or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion. In certain embodiments, introgression could thus be achieved by substitution of a locus not associated with tolerance to low iron growth conditions with a corresponding locus that is associated with low iron growth condition tolerance or by conversion of a locus from a non-tolerant genotype to a tolerant genotype.

As used herein, "linkage" refers to relative frequency at which types of gametes are produced in a cross. For example, if locus A has genes "A" or "a" and locus B has genes "B" or "b," then a cross between parent 1 with AABB and parent 2 with aabb can produce four possible gametes segregating into AB, Ab, aB and ab genotypes. The null expectation is that there will be independent equal segregation into each of the four possible genotypes, i.e. no linkage between locus A and locus B results in ¼ of the gametes from each genotype (AB, Ab, aB, and ab). Segregation of gametes into genotype ratios differing from ¼ indicates linkage between locus A and locus B. As used herein, linkage can be between two markers, or alternatively between a marker and a phenotype. A marker locus can be associated with (linked to) a trait, e.g., a marker locus can be associated with tolerance or improved tolerance to a plant pathogen when the marker locus is in linkage disequilibrium (LD) with the tolerance trait. The degree of linkage of a molecular marker to a phenotypic trait (e.g., a QTL) is measured, e.g., as a statistical probability of co-segregation of that molecular marker with the phenotype.

As used herein, the linkage relationship between a molecular marker and a phenotype is given is the statistical likelihood that the particular combination of a phenotype and the presence or absence of a particular marker allele is random. Thus, the lower the probability score, the greater the likelihood that a phenotype and a particular marker will cosegregate. In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p<0.5). For example, a significant probability can be less than 0.25, less than 0.20, less than 0.15, or less than 0.1.

As used herein, the term "linked" or "genetically linked," when used in the context of markers and/or genomic regions, means that recombination between two linked loci occurs with a frequency of equal to or less than about 10% (i.e., are separated on a genetic map by not more than 10 cM). In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 20, 19, 18, 17, 16, 15, 14, 13, 12, 11, 10, 9, 8, 7, 6, 5, 4, 3, 2, 1, 0.75, 0.5 or 0.25 cM or less from each other.

As used herein, "marker," "genetic marker," "molecular marker," and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide, and can be represented by one or more particular variant sequences, or by a consensus sequence. In another sense, a marker is an isolated variant or consensus of such a sequence. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus.

As used herein, "marker assay" means a method for detecting a polymorphism at a particular locus using a particular method. Marker assays thus include, but are not limited to, measurement of at least one phenotype (such as disease resistance, seed color, flower color, or other visually detectable trait as well as any biochemical trait), restriction fragment length polymorphism (RFLP), single base extension, electrophoresis, sequence alignment, allelic specific oligonucleotide hybridization (ASO), random amplified polymorphic DNA (RAPD), microarray-based polymorphism detection technologies, and the like.

As used herein, "phenotype" means the detectable characteristics of a cell or organism which can be influenced by gene expression.

As used herein, a "nucleic acid molecule," of naturally occurring origins or otherwise, may be an "isolated" nucleic acid molecule. An isolated nucleic acid molecule is one removed from its native cellular and chromosomal environment. The term "isolated" is not intended to encompass molecules present in their native state. If desired, an isolated nucleic acid may be substantially purified, meaning that it is the predominant species present in a preparation. A substantially purified molecule may be at least about 60% free, preferably at least about 75% free, more preferably at least about 90% free, and most preferably at least about 95% free from the other molecules (exclusive of solvent) present in the preparation.

As used herein, "quantitative trait locus (QTL)" means a genetic domain that effects a phenotype that can be described in quantitative terms and can be assigned a "phenotypic value" which corresponds to a quantitative value for the phenotypic trait. A QTL can act through a single gene mechanism or by a polygenic mechanism. In some aspects, the invention provides QTL genomic regions, where a QTL (or multiple QTLs) that segregates with low iron tolerance is contained in those regions. In one embodiment of this invention, the boundaries of genomic regions are drawn to encompass markers that will be linked to one or more QTL. In other words, the chromosome interval is drawn such that any marker that lies within that region (including the terminal markers that define the boundaries of the region) is genetically linked to the QTL. Each region comprises at least one QTL, and furthermore, may indeed comprise more than one QTL. Close proximity of multiple QTL in the same region may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTL. Regardless, knowledge of how many QTL are in a particular interval is not necessary to make or practice the invention.

As used herein, the term "soybean" means *Glycine max* and includes all plant varieties that can be bred with soybean, including wild soybean species. In certain embodiments, soybean plants from the species *Glycine max* and the subspecies *Glycine max* L. ssp. *max* or *Glycine max* ssp. *formosana* can be genotyped using the compositions and methods of the present invention. In an additional aspect, the soybean plant is from the species *Glycine soja*, otherwise known as wild soybean, can be genotyped using these compositions and methods. Alternatively, soybean germplasm derived from any of *Glycine max*, *Glycine max* L. ssp. *max*, *Glycine max* ssp. *Formosana*, and/or *Glycine soja* can be genotyped using compositions and methods provided herein.

As used herein, the term "single nucleotide polymorphism," also referred to by the abbreviation "SNP," means a polymorphism at a single site wherein the polymorphism constitutes any or all of a single base pair change, an insertion of one or more base pairs, and/or a deletion of one or more base pairs.

As used herein, the phrases "low iron," "low-available iron," "low soluble iron," "low iron conditions," "low iron growth conditions," "iron shortage" or "iron deficiency" or the like refer to conditions where iron availability is less than optimal for soybean growth, and can cause plant pathology, e.g., IDC, due to the lack of metabolically-available iron. It is recognized that under "iron deficient" conditions, the absolute concentration of atomic iron may be sufficient, but the form of the iron (e.g., its incorporation into various molecular structures) and other environmental factors may make the iron unavailable for plant use. For example, high carbonate levels, high pH, high salt content, herbicide applications, cool temperatures, saturated soils, or other environmental factors can decrease iron solubility, and reduce the solubilized forms of iron that the plant requires for uptake. One of skill in the art is familiar with assays to measure iron content of soil, as well as those concentrations of iron that are optimal or sub-optimal for plant growth.

As used herein, the terms "tolerance" or "improved tolerance" in reference to a soybean plant grown in low iron growth conditions is an indication that the soybean plant is less affected by the low-available iron conditions with respect to yield, survivability and/or other relevant agronomic measures, compared to a less tolerant, more "susceptible" plant. Tolerance is a relative term, indicating that a tolerant" plant survives and/or produces better yield of soybean in low-available iron growth conditions compared to a different (less tolerant) plant (e.g., a different soybean strain) grown in similar low-available iron conditions. That is, the low-available iron growth conditions cause a reduced decrease in soybean survival and/or yield in a tolerant soybean plant, as compared to a susceptible soybean plant. As used in the art, iron-deficiency "tolerance" is sometimes used interchangeably with iron-deficiency "resistance."

One of skill will appreciate that soybean plant tolerance to low-available iron conditions varies widely, and can represent a spectrum of more-tolerant or less-tolerant phenotypes. However, by simple observation, one of skill can generally determine the relative tolerance or susceptibility of different plants, plant lines or plant families under low-available iron conditions, and furthermore, will also recognize the phenotypic gradations of "tolerant."

In one example, a plant's tolerance can be approximately quantitated using a chlorosis scoring system. In such a system, a plant that is grown in a known iron-deficient area, or in low-available iron experimental conditions, and is assigned a tolerance rating of between 1 (highly susceptible; most or all plants dead; those that live are stunted and have little living tissue) to 9 (highly tolerant; yield and survivability not significantly affected; all plants normal green color). See also, Dahiya and Singh (1979) "Effect of salinity, alkalinity and iron sources on availability of iron," Plant and Soil 51:13-18.

II. Description of the Invention: Overview

In accordance with the present invention, Applicants have discovered genomic regions, associated markers, and associated methods for identifying and associating genotypes that affect an iron deficient growth condition tolerance trait.

The advent of molecular genetic markers has facilitated mapping and selection of agriculturally important traits in soybean. Markers tightly linked to tolerance genes are an asset in the rapid identification of tolerant soybean lines on the basis of genotype by the use of marker assisted selection (MAS). Introgressing tolerance genes into a desired cultivar is also facilitated by using suitable nucleic acid markers.

The use of markers to infer a phenotype of interest results in the economization of a breeding program by substituting costly, time-intensive phenotyping assays with genotyping assays. Further, breeding programs can be designed to explicitly drive the frequency of specific, favorable phenotypes by targeting particular genotypes (U.S. Pat. No. 6,399,855). Fidelity of these associations may be monitored continuously to ensure maintained predictive ability and, thus, informed breeding decisions (U.S. Patent Application 2005/0015827). In this case, costly, time-intensive phenotyping assays required for determining if a plant or plants contains a genomic region associated with a low iron growth condition tolerant phenotype can be supplanted by genotypic assays that provide for identification of a plant or plants that contain the desired genomic region.

III. QTL Associated with Tolerance to Low Iron Growth Conditions

Provided herewith are certain other QTL that have also been identified as associated with a desirable phenotype of tolerance to growth in low iron conditions when present in certain allelic forms.

These several soybean QTL provided—that can be associated with a desirable low iron growth condition tolerant phenotype when present in certain allelic forms—are located on soybean chromosome 16 (soybean linkage group J), soybean chromosome 15 (soybean linkage group E), soybean chromosome 7 (soybean linkage group M), soybean chromosome 17 (soybean linkage group D2), and soybean chromosome 10 (soybean linkage group O).

Tables 1, 3, 5, 7, 9 (corresponding to chromosomes 16, 15, 7, 17, and 10, respectively) shows the relative positions of certain markers that have been disclosed in public databases and non-public (bolded) polymorphic nucleic acid markers, designated SEQ ID NOs, genetic positions (cM) on the chromosome, the allelic forms of certain polymorphic nucleic acid markers associated with a low iron growth condition tolerant phenotype, the allelic forms of those polymorphic nucleic acid markers not associated with the low iron growth condition tolerant phenotype, and the polymorphic position within the sequence of the polymorphic nucleic acid marker. The bolded markers have been identified as within a genomic region associated with a low iron growth condition tolerant phenotype.

Tables 2, 4, 6, 8, 10 (corresponding to chromosomes 16, 15, 7, 17, and 10, respectively) provides for each polymorphic nucleic acid marker/SEQ ID NO: the linkage group corresponding to the chromosome and the relative physical map positions of the markers.

TABLE 1

Chromosome 16-QTL on chromosome 16 associated with a low iron growth condition tolerant phenotype.

| Marker Locus Name/SEQ ID NO. | cM Map Position on Chromosome Sixteen (16) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|
| asmbl_10470 | * | * | * | * | |
| BI427060 | * | * | * | * | * |
| 1 | 104.6 | 3.2 | GG | AA | 201 |
| 2 | 104.9 | 3.9 | CC | GG | 201 |
| 3 | 105.2 | 2.9 | GG | AA | 201 |
| 4 | 105.5 | 3.9 | CC | AA | 281 |
| 5 | 105.6 | 3.2 | CC | TT | 618 |
| 6 | 105.6 | 2.8 | CC | AA | 201 |
| 7 | 105.7 | 3.0 | CC | TT | 201 |
| 8 | 106.2 | 2.9 | CC | TT | 201 |
| 9 | 106.3 | 3.1 | GG | CC | 201 |
| 10 | 106.4 | 3.8 | CC | TT | 201 |
| 11 | 107.1 | 3.6 | AA | CC | 201 |
| 12 | 107.2 | 3.2 | GG | CC | 201 |
| 13 | 107.3 | 2.7 | AA | GG | 201 |
| 14 | 107.6 | 3.6 | GG | AA | 201 |
| 15 | 107.6 | 2.5 | CC | TT | 176 |
| 16 | 107.9 | 2.5 | CC | TT | 201 |
| 17 | 108.5 | 2.7 | CC | TT | 201 |

TABLE 1-continued

Chromosome 16-QTL on chromosome 16 associated with a low iron growth condition tolerant phenotype.

| Marker Locus Name/SEQ ID NO. | cM Map Position on Chromosome Sixteen (16) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|
| 18 | 108.8 | 3.3 | TT | CC | 201 |
| 19 | 108.8 | 2.6 | CC | TT | 201 |
| 20 | 108.8 | 3.0 | AA | CC | 925 |
| 21 | 109.5 | 2.2 | TT | CC | 201 |
| 22 | 109.8 | 2.4 | TT | AA | 380 |
| 23 | 110.1 | 2.5 | GG | AA | 201 |
| 24 | 110.5 | 4.0 | TT | AA | 201 |
| 25 | 110.8 | 4.3 | CC | AA | 639 |
| 26 | 113.8 | 3.3 | TT | AA | 123 |
| 27 | 111.1 | 5.0 | CC | TT | 201 |
| 28 | 111.3 | 2.5 | TT | CC | 201 |
| 29 | 111.4 | 2.4 | TT | CC | 201 |
| 30 | 111.5 | 2.8 | CC | AA | 201 |
| 31 | 111.7 | 3.7 | AA | GG | 201 |
| 32 | 112 | 2.8 | AA | GG | 201 |
| 33 | 112.1 | 2.6 | GG | CC | 201 |
| 34 | 112.3 | 4.4 | AA | GG | 201 |
| 35 | 112.6 | 3.3 | CC | AA | 201 |
| 36 | 112.8 | 3.1 | TT | CC | 347 |
| 37 | 112.9 | 2.9 | TT | CC | 201 |
| 38 | 113.1 | 2.8 | AA | GG | 201 |
| 39 | 113.4 | 2.9 | TT | GG | 201 |
| 40 | 113.6 | 2.6 | TT | CC | 201 |
| 41 | 113.7 | 2.7 | CC | TT | 201 |
| 42 | 113.7 | 2.8 | TT | CC | 155 |
| 43 | 113.7 | 3.0 | AA | GG | 261 |
| 44 | 113.8 | 2.4 | TT | CC | 201 |
| 45 | 113.8 | 2.3 | AA | GG | 194 |
| 46 | 113.9 | 2.7 | GG | TT | 201 |
| 47 | 114.1 | 2.4 | TT | CC | 201 |
| 48 | 114.4 | 2.4 | TT | CC | 285 |
| TA67482_3847 | * | * | * | * | * |
| TC370075 | * | * | * | * | * |

TABLE 2

Chromosome 16 - Physical positions of certain genetic markers on soybean chromosome 16 in proximity to QTL associated with a low iron growth condition tolerant phenotype.

| Marker Locus Name/SEQ ID NO. | Linkage Group | Chromosome | Middle Position | Start Position | End Position |
|---|---|---|---|---|---|
| asmbl_10470 | J | 16 | 31363336 | 31362972 | 31363701 |
| BI427060 | J | 16 | 31363515 | 31363238 | 31363792 |
| 1 | J | 16 | 31369584 | 31369434 | 31369735 |
| 2 | J | 16 | 31443226 | 31443076 | 31443377 |
| 3 | J | 16 | 31477826 | 31478015 | 31477638 |
| 4 | J | 16 | 31480456 | 31480836 | 31480077 |
| 5 | J | 16 | 31486792 | 31486642 | 31486943 |
| 6 | J | 16 | 31480983 | 31480833 | 31481134 |
| 7 | J | 16 | 31510525 | 31510375 | 31510676 |
| 8 | J | 16 | 31516209 | 31516059 | 31516360 |
| 9 | J | 16 | 31521798 | 31521648 | 31521949 |
| 10 | J | 16 | 31553067 | 31552917 | 31553218 |
| 11 | J | 16 | 31557341 | 31557191 | 31557492 |
| 12 | J | 16 | 31563379 | 31563229 | 31563530 |
| 13 | J | 16 | 31574585 | 31574435 | 31574736 |
| 14 | J | 16 | 31575341 | 31575137 | 31575545 |
| 15 | J | 16 | 31577004 | 31576854 | 31577155 |
| 16 | J | 16 | 31580785 | 31580635 | 31580936 |
| 17 | J | 16 | 31614520 | 31614370 | 31614671 |
| 18 | J | 16 | 31614870 | 31615435 | 31614305 |
| 19 | J | 16 | 31618039 | 31617889 | 31618190 |
| 20 | J | 16 | 31643780 | 31643630 | 31643931 |
| 21 | J | 16 | 31785190 | 31785040 | 31785341 |
| 22 | J | 16 | 31804506 | 31804356 | 31804657 |
| 23 | J | 16 | 31831923 | 31831773 | 31832074 |
| 24 | J | 16 | 31889649 | 31889499 | 31889800 |
| 25 | J | 16 | 31904942 | 31904792 | 31905093 |
| 26 | J | 16 | 31911271 | 31911121 | 31911422 |
| 27 | J | 16 | 31925976 | 31925826 | 31926127 |
| 28 | J | 16 | 31952216 | 31952066 | 31952367 |
| 29 | J | 16 | 31990398 | 31990248 | 31990549 |
| 30 | J | 16 | 31997204 | 31997054 | 31997355 |
| 31 | J | 16 | 32031978 | 32031828 | 32032129 |
| 32 | J | 16 | 32079262 | 32079112 | 32079413 |
| 33 | J | 16 | 32100628 | 32100039 | 32101218 |
| 34 | J | 16 | 32154510 | 32154694 | 32154327 |
| 35 | J | 16 | 32161907 | 32161757 | 32162058 |
| 36 | J | 16 | 32204175 | 32204025 | 32204326 |
| 37 | J | 16 | 32242461 | 32242311 | 32242612 |
| 38 | J | 16 | 32279082 | 32278743 | 32279421 |
| 39 | J | 16 | 32291528 | 32291900 | 32291157 |
| 40 | J | 16 | 32347306 | 32347156 | 32347457 |
| 41 | J | 16 | 32434829 | 32446198 | 32423461 |
| 42 | J | 16 | 32484745 | 32484595 | 32484896 |
| 43 | J | 16 | 32519227 | 32519077 | 32519378 |
| 44 | J | 16 | 32672805 | 32672655 | 32672956 |
| 45 | J | 16 | 32852516 | 32852366 | 32852667 |
| 46 | J | 16 | 32852826 | 32852442 | 32853211 |
| 47 | J | 16 | 32854325 | 32854591 | 32854059 |
| 48 | J | 16 | 31374689 | 31374539 | 31374840 |
| TA67482_3847 | J | 16 | 32859166 | 32858544 | 32859789 |
| TC370075 | J | 16 | 32859832 | 32859787 | 32859877 |

TABLE 3

Chromosome 15-QTL on chromosome 15 associated with a low iron growth condition tolerant phenotype.

| Marker Locus Name/SEQ ID NO. | cM Map Position on Chromosome Fifteen (15) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|
| DB975811 | * | * | * | * | * |
| TA67841_3847 | * | * | * | * | * |
| 49 | 22.5 | 3.0 | TT | CC | 201 |
| 50 | 22.7 | 4.1 | CC | TT | 201 |
| 51 | 22.9 | 3.1 | CC | GG | 201 |
| 52 | 23.6 | 3.4 | TT | CC | 201 |
| 53 | 23.7 | 3.6 | CC | TT | 201 |
| 54 | 23.9 | 3.4 | TT | GG | 354 |
| 55 | 23.9 | 4.1 | CC | CC | 355 |
| 56 | 24.1 | 3.2 | TT | AA | 61 |
| 57 | 24.7 | 4.1 | AA | GG | 201 |
| 58 | 24.7 | 4.1 | GG | AA | 240 |
| 59 | 24.7 | 4.1 | GG | AA | 428 |
| 60 | 24.9 | 3.3 | CC | TT | 993 |

TABLE 3-continued

Chromosome 15-QTL on chromosome 15 associated with a low iron growth condition tolerant phenotype.

| Marker Locus Name/SEQ ID NO. | cM Map Position on Chromosome Fifteen (15) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|
| 61 | 25.4 | 3.9 | TT | CC | 201 |
| 62 | 25.6 | 5.6 | TT | CC | 201 |
| 63 | 26.4 | 3.9 | CC | AA | 201 |
| 64 | 31.4 | 3.0 | TT | CC | 201 |
| 65 | 31.6 | 3.0 | TT | GG | 201 |
| 66 | 31.7 | 3.1 | AA | GG | 201 |
| 67 | 31.8 | 4.6 | GG | AA | 201 |
| 68 | 32.4 | 3.1 | AA | GG | 201 |
| 69 | 32.5 | 3.3 | GG | AA | 201 |
| TC370174 | * | * | * | * | * |
| Glyma15g06010 | * | * | * | * | * |

TABLE 4

Chromosome 15 - Physical positions of certain genetic markers on soybean chromosome 5 in proximity to QTL associated with a low iron growth condition tolerant phenotype.

| Marker Locus Name/SEQ ID NO. | Linkage Group | Chromosome | Middle Position | Start Position | End Position |
|---|---|---|---|---|---|
| DB975811 | E | 15 | 2656905 | 2656345 | 2657466 |
| TA67841_3847 | E | 15 | 2656990 | 2656430 | 2657551 |
| 49 | E | 15 | 2657551 | 2657401 | 2657702 |
| 50 | E | 15 | 2674098 | 2673948 | 2674249 |
| 51 | E | 15 | 2701610 | 2701460 | 2701761 |
| 52 | E | 15 | 2796176 | 2796026 | 2796327 |
| 53 | E | 15 | 2822719 | 2822569 | 2822870 |
| 54 | E | 15 | 2847164 | 2847410 | 2846919 |
| 55 | E | 15 | 2847207 | 2847057 | 2847358 |
| 56 | E | 15 | 3039453 | 3039024 | 3039882 |
| 57 | E | 15 | 3043572 | 3043814 | 3043331 |
| 58 | E | 15 | 3048934 | 3048784 | 3049085 |
| 59 | E | 15 | 3154544 | 3154394 | 3154695 |
| 60 | E | 15 | 3178097 | 3177947 | 3178248 |
| 61 | E | 15 | 3301037 | 3300887 | 3301188 |
| 62 | E | 15 | 3402856 | 3402706 | 3403007 |
| 63 | E | 15 | 3756773 | 3756509 | 3757037 |
| 64 | E | 15 | 2662233 | 2662435 | 2662031 |
| 65 | E | 15 | 2663725 | 2663953 | 2663497 |
| 66 | E | 15 | 2667350 | 2667200 | 2667501 |
| 67 | E | 15 | 2697692 | 2697542 | 2697843 |
| 68 | E | 15 | 2722948 | 2722798 | 2723099 |
| 69 | E | 15 | 2729212 | 2729062 | 2729363 |
| TC370174 | E | 15 | 2772449 | 2772299 | 2772600 |
| Glyma15g06010 | E | 15 | 2790560 | 2790410 | 2790711 |

TABLE 5

Chromosome 7-QTL on chromosome 7 associated with a low iron growth condition tolerant phenotype.

| Marker Locus Name/SEQ ID NO. | cM Map Position on Chromosome Seven (7) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|
| TA75172_3847 | * | * | * | * | * |
| Contig4349 | * | * | * | * | * |

TABLE 5-continued

Chromosome 7-QTL on chromosome 7 associated with a low iron growth condition tolerant phenotype.

| Marker Locus Name/SEQ ID NO. | cM Map Position on Chromosome Seven (7) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|
| 70 | 46.7 | 1.5 | AA | GG | 201 |
| 71 | 51.8 | 1.5 | AA | GG | 650 |
| 72 | 53.5 | 1.9 | AA | TT | 201 |
| 73 | 53.7 | 2.0 | TT | GG | 201 |
| 74 | 54.5 | 1.8 | GG | TT | 201 |
| 75 | 58.6 | 1.4 | GG | AA | 201 |
| 76 | 58.9 | 1.5 | GG | AA | 201 |
| 77 | 59.6 | 1.4 | TT | CC | 201 |
| 78 | 59.7 | 2.4 | GG | AA | 201 |
| 79 | 59.8 | 2.1 | TT | CC | 201 |
| 80 | 96.4 | 3.0 | TT | CC | 201 |
| 81 | 98.2 | 3.0 | GG | CC | 201 |
| 82 | 98.6 | 3.2 | TT | CC | 201 |
| 83 | 102.1 | 2.3 | GG | AA | 201 |
| 84 | 102.8 | 2.2 | AA | GG | 201 |
| 85 | 102.9 | 2.2 | AA | GG | 201 |
| AW705305 | * | * | * | * | * |
| TC380682 | * | * | * | * | * |

TABLE 6

Chromosome 7 - Physical positions of certain genetic markers on soybean chromosome 7 in proximity to QTL associated with a low iron growth condition tolerant phenotype.

| Marker Locus Name/SEQ ID NO. | Linkage Group | Chromosome | Middle Position | Start Position | End Position |
|---|---|---|---|---|---|
| TA75172_3847 | M | 7 | 5421539 | 5421375 | 5421704 |
| Contig4349 | M | 7 | 5422610 | 5422460 | 5422761 |
| 70 | M | 7 | 6777792 | 6777642 | 6777943 |
| 71 | M | 7 | 6814309 | 6814159 | 6814460 |
| 72 | M | 7 | 6911064 | 6910914 | 6911215 |
| 73 | M | 7 | 7602143 | 7601993 | 7602294 |
| 74 | M | 7 | 7671547 | 7671397 | 7671698 |
| 75 | M | 7 | 7801323 | 7801173 | 7801474 |
| 76 | M | 7 | 7821649 | 7821499 | 7821800 |
| 77 | M | 7 | 7829639 | 7829489 | 7829790 |
| 78 | M | 7 | 17390045 | 17389895 | 17390196 |
| 79 | M | 7 | 17724916 | 17724766 | 17725067 |
| 80 | M | 7 | 17812664 | 17812514 | 17812815 |
| 81 | M | 7 | 18464522 | 18464372 | 18464673 |
| 82 | M | 7 | 18592542 | 18592392 | 18592693 |
| 83 | M | 7 | 18594332 | 18594182 | 18594483 |
| 84 | M | 7 | 18592542 | 18592392 | 18592693 |
| 85 | M | 7 | 18594332 | 18594182 | 18594483 |
| AW705305 | M | 7 | 18594647 | 18594463 | 18594831 |
| TC380682 | M | 7 | 18594649 | 18594451 | 18594848 |

TABLE 7

Chromosome 17-QTL on chromosome 17 associated with a low iron growth condition tolerant phenotype.

| Marker Locus Name/SEQ ID NO. | cM Map Position on Chromosome Seventeen (17) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|
| TC350035 | * | * | * | * | * |
| TA43074_3847 | * | * | * | * | * |
| 86 | 5.2 | 2.0 | GG | TT | 201 |
| 87 | 5.4 | 2.0 | TT | GG | 201 |
| 88 | 5.6 | 3.2 | CC | TT | 201 |
| 89 | 5.7 | 3.3 | AA | TT | 201 |
| 90 | 5.8 | 3.2 | TT | GG | 201 |
| 91 | 5.8 | 3.3 | AA | GG | 201 |
| 92 | 5.9 | 3.1 | GG | CC | 201 |
| 93 | 6 | 3.2 | TT | GG | 201 |
| 94 | 6.1 | 3.1 | GG | AA | 201 |
| 95 | 6.3 | 3.1 | AA | CC | 201 |
| 96 | 6.5 | 3.1 | AA | TT | 201 |
| 97 | 6.6 | 3.0 | TT | AA | 201 |
| 98 | 6.8 | 3.0 | GG | AA | 201 |
| 99 | 7.1 | 3.0 | GG | CC | 439 |
| 100 | 7.3 | 3.0 | CC | TT | 201 |
| 101 | 7.5 | 2.4 | CC | GG | 201 |
| 102 | 7.7 | 2.4 | CC | AA | 201 |
| 103 | 8 | 3.2 | AA | TT | 201 |
| 104 | 8.1 | 3.0 | GG | AA | 201 |
| 105 | 8.2 | 2.8 | TT | CC | 201 |
| 106 | 8.2 | 2.7 | GG | AA | 201 |
| 107 | 8.4 | 2.7 | TT | CC | 201 |
| 108 | 8.5 | 2.8 | CC | TT | 201 |
| 109 | 8.8 | 3.0 | TT | CC | 201 |
| 110 | 9 | 2.8 | AA | CC | 201 |
| 111 | 9.2 | 3.5 | TT | GG | 201 |
| 112 | 9.3 | 3.6 | TT | AA | 201 |
| Glyma17g01380 | * | * | * | * | * |
| Gm_W82_CR17.G8870 | * | * | * | * | * |

TABLE 8

Chromosome 17 - Physical positions of certain genetic markers on soybean chromosome 17 in proximity to QTL associated with a low iron growth condition tolerant phenotype.

| Marker Locus Name/ SEQ ID NO | Linkage Group | Chromosome | Middle Position | Start Position | End Position |
|---|---|---|---|---|---|
| TC350035 | D2 | 17 | 280819 | 279005 | 282633 |
| TA43074_3847 | D2 | 17 | 280856 | 279080 | 282633 |
| 86 | D2 | 17 | 282695 | 282545 | 282846 |
| 87 | D2 | 17 | 317160 | 317010 | 317311 |
| 88 | D2 | 17 | 342956 | 342806 | 343107 |
| 89 | D2 | 17 | 349222 | 349072 | 349373 |
| 90 | D2 | 17 | 358930 | 358780 | 359081 |
| 91 | D2 | 17 | 368357 | 368207 | 368508 |
| 92 | D2 | 17 | 384568 | 384418 | 384719 |
| 93 | D2 | 17 | 397053 | 396903 | 397204 |
| 94 | D2 | 17 | 408927 | 408777 | 409078 |
| 95 | D2 | 17 | 435118 | 434968 | 435269 |
| 96 | D2 | 17 | 464163 | 464013 | 464314 |
| 97 | D2 | 17 | 479395 | 479245 | 479546 |
| 98 | D2 | 17 | 495991 | 495841 | 496142 |
| 99 | D2 | 17 | 545090 | 544843 | 545337 |
| 100 | D2 | 17 | 574773 | 574623 | 574924 |
| 101 | D2 | 17 | 602079 | 601929 | 602230 |
| 102 | D2 | 17 | 618344 | 618194 | 618495 |
| 103 | D2 | 17 | 670615 | 670465 | 670766 |
| 104 | D2 | 17 | 683816 | 683666 | 683967 |
| 105 | D2 | 17 | 685126 | 684976 | 685277 |
| 106 | D2 | 17 | 693456 | 693306 | 693607 |
| 107 | D2 | 17 | 717263 | 717113 | 717414 |
| 108 | D2 | 17 | 732375 | 732225 | 732526 |
| 109 | D2 | 17 | 782062 | 781912 | 782213 |
| 110 | D2 | 17 | 809659 | 809509 | 809810 |
| 111 | D2 | 17 | 823632 | 823482 | 823783 |
| 112 | D2 | 17 | 840172 | 840022 | 840323 |
| Glyma17g01380 | D2 | 17 | 844200 | 842706 | 845694 |
| Gm_W82_CR17.G8870 | D2 | 17 | 844200 | 842706 | 845694 |

TABLE 9

Chromosome 10-QTL on chromosome 10 associated with a low iron growth condition tolerant phenotype.

| Marker Locus Name/SEQ ID NO. | cM Map Position on Chromosome Seventeen (10) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|
| NA | * | * | * | * | * |
| WmFPC_Contig227 | * | * | * | * | * |
| 113 | 85.9 | 2.4 | TT | CC | 201 |
| 114 | 86.3 | 2.7 | CC | TT | 201 |
| 115 | 86.6 | 2.5 | AA | GG | 201 |
| 116 | 86.7 | 2.6 | CC | TT | 201 |
| 117 | 86.8 | 2.3 | CC | GG | 201 |
| 118 | 86.9 | 2.6 | GG | AA | 201 |
| 119 | 87.2 | 2.5 | CC | TT | 201 |
| 120 | 87.3 | 2.7 | TT | AA | 201 |
| 121 | 87.4 | 2.4 | GG | AA | 201 |
| 122 | 87.5 | 2.2 | CC | TT | 201 |
| 123 | 87.6 | 2.8 | CC | TT | 201 |
| 124 | 87.7 | 2.9 | CC | TT | 201 |
| 125 | 87.8 | 2.7 | GG | AA | 136 |
| 126 | 88 | 2.5 | TT | GG | 201 |
| 127 | 88.1 | 2.6 | CC | TT | 219 |
| 128 | 89.7 | 2.5 | AA | GG | 201 |
| 129 | 89.8 | 2.5 | GG | AA | 201 |
| 130 | 90.1 | 2.7 | AA | TT | 201 |

TABLE 9-continued

Chromosome 10-QTL on chromosome 10 associated with a low iron growth condition tolerant phenotype.

| Marker Locus Name/SEQ ID NO. | cM Map Position on Chromosome Seventeen (10) | [-LOG10(P)] | Allelic Form(s) Associated With Low Fe Tolerance Phenotype[1] | Allelic Form(s) Not-Associated with Low Fe Tolerance Phenotype[1] | Polymorphic Position |
|---|---|---|---|---|---|
| 131 | 90.9 | 2.8 | TT | CC | 201 |
| 132 | 91.2 | 3.7 | AA | GG | 201 |
| 133 | 91.3 | 2.8 | AA | CC | 201 |
| 134 | 91.4 | 2.1 | GG | CC | 201 |
| 135 | 91.5 | 3.9 | AA | GG | 201 |
| 136 | 91.7 | 2.2 | TT | GG | 201 |
| 137 | 91.9 | 3.9 | TT | AA | 201 |
| 138 | 92 | 3.7 | GG | AA | 201 |
| 139 | 92.1 | 3.7 | CC | AA | 201 |
| 140 | 92.2 | 3.7 | GG | AA | 201 |
| 141 | 92.4 | 3.9 | TT | CC | 201 |
| 142 | 93.9 | 2.1 | GG | CC | 201 |
| 143 | 94.3 | 2.1 | GG | AA | 201 |
| 144 | 94.4 | 2.1 | TT | CC | 201 |
| 145 | 94.5 | 2.1 | CC | AA | 201 |
| 146 | 95.8 | 2.4 | TT | AA | 201 |
| 147 | 101 | 2.1 | CC | TT | 201 |
| Glyma10g28920 | * | * | * | * | * |
| Cf16144d | * | * | * | * | * |

TABLE 10

Chromosome 10 - Physical positions of certain genetic markers on soybean chromosome 10 in proximity to QTL associated with a low iron growth condition tolerant phenotype.

| Marker Locus Name/SEQ ID NO | Linkage Group | Chromosome | Middle Position | Start Position | End Position |
|---|---|---|---|---|---|
| NA | O | 10 | 29358961 | 11677282 | 47040641 |
| WmFPC_Contig227 | O | 10 | 29398139 | 28618646 | 30177632 |
| 113 | O | 10 | 29720865 | 29720715 | 29721016 |
| 114 | O | 10 | 30158032 | 30157882 | 30158183 |
| 115 | O | 10 | 30164795 | 30164645 | 30164946 |
| 116 | O | 10 | 30168646 | 30168496 | 30168797 |
| 117 | O | 10 | 30173472 | 30173322 | 30173623 |
| 118 | O | 10 | 30197793 | 30197643 | 30197944 |
| 119 | O | 10 | 30250601 | 30250451 | 30250752 |
| 120 | O | 10 | 30265182 | 30265032 | 30265333 |
| 121 | O | 10 | 30296454 | 30296304 | 30296605 |
| 122 | O | 10 | 30302927 | 30302777 | 30303078 |
| 123 | O | 10 | 30338781 | 30338631 | 30338932 |
| 124 | O | 10 | 30339883 | 30339733 | 30340034 |
| 125 | O | 10 | 30368472 | 30368234 | 30368710 |
| 126 | O | 10 | 30785142 | 30784992 | 30785293 |
| 127 | O | 10 | 30923459 | 30923014 | 30923904 |

TABLE 10-continued

Chromosome 10 - Physical positions of certain genetic markers on soybean chromosome 10 in proximity to QTL associated with a low iron growth condition tolerant phenotype.

| Marker Locus Name/SEQ ID NO | Linkage Group | Chromosome | Middle Position | Start Position | End Position |
|---|---|---|---|---|---|
| 128 | O | 10 | 36092106 | 36091956 | 36092257 |
| 129 | O | 10 | 36297861 | 36297711 | 36298012 |
| 130 | O | 10 | 37237431 | 37237281 | 37237582 |
| 131 | O | 10 | 37349903 | 37349753 | 37350054 |
| 132 | O | 10 | 37364859 | 37364709 | 37365010 |
| 133 | O | 10 | 37381677 | 37381527 | 37381828 |
| 134 | O | 10 | 37396158 | 37396008 | 37396309 |
| 135 | O | 10 | 37396896 | 37396746 | 37397047 |
| 136 | O | 10 | 37428843 | 37428693 | 37428994 |
| 137 | O | 10 | 37453860 | 37453710 | 37454011 |
| 138 | O | 10 | 37465158 | 37465008 | 37465309 |
| 139 | O | 10 | 37479303 | 37479153 | 37479454 |
| 140 | O | 10 | 37492059 | 37491909 | 37492210 |
| 141 | O | 10 | 37525000 | 37524850 | 37525151 |
| 142 | O | 10 | 37718944 | 37718794 | 37719095 |
| 143 | O | 10 | 37753981 | 37753831 | 37754132 |
| 144 | O | 10 | 37761477 | 37761327 | 37761628 |
| 145 | O | 10 | 37763485 | 37763284 | 37763687 |
| 146 | O | 10 | 37898074 | 37897924 | 37898225 |
| 147 | O | 10 | 38394420 | 38394270 | 38394571 |
| Glyma10g28920 | O | 10 | 38395822 | 38395602 | 38396043 |
| Cf16144d | O | 10 | 38397079 | 38396831 | 38397328 |

IV. Identification of Plants Exhibiting Tolerance to Low Iron Growth Conditions To observe the presence or absence of low iron growth condition tolerant phenotypes, soybean plants comprising genotypes of interest can be exposed to low iron or iron deficient growth conditions in seedling stages, early to mid-vegetative growth stages, or in early reproductive stages. Experienced plant breeders can recognize tolerant soybean plants in the field, and can select the tolerant individuals or populations for breeding purposes or for propagation. In this context, the plant breeder recognizes "tolerant" and "susceptible" soybean plants in fortuitous naturally-occurring filed observations.

Breeders will appreciate that plant tolerance is a phenotypic spectrum consisting of extremes in tolerance, susceptibility, and a continuum of intermediate phenotypes. Tolerance also varies due to environmental effects. Evaluation of phenotypes using reproducible assays and tolerance scoring methods are of value to scientists who seek to identify genetic loci that impart tolerance, conduct marker assisted selection to create tolerant soybean populations, and for introgression techniques to breed a tolerance trait into an elite soybean line, for example.

In contrast to fortuitous field observations that classify plants as either "tolerant" or "susceptible," various methods are known in the art for determining (and quantitating) the tolerance of a soybean plant to iron-deficient growth conditions. These techniques can be applied to different fields at different times, or to experimental greenhouse or laboratory settings, and provide approximate tolerance scores that can be used to characterize the tolerance of a given strain or line regardless of growth conditions or location. See, for example, Diers et al. (1992) "Possible identification of quantitative trait loci affecting iron efficiency in soybean," J. Plant Nutr. 15:217-2136; Dahiya and M. Singh (1979) "Effect of salinity, alkalinity and iron sources on availability of iron," Plant and Soil 51:13-18; and Gonzalez-Vallejo et al. (2000) "Iron Deficiency Decreases the Fe(III)-Chelate Reducing Activity of Leaf Protoplasts" Plant Physiol. 122 (2): 337-344.

The degree of IDC in a particular plant or stand of plants can be quantitated by using a system to score the severity of the disease in each plant. A plant strain or variety or a number of plant strains or varieties are planted and grown in a single stand in soil that is known to produce chlorotic plants as a result of iron deficiency ("field screens," i.e., in fields that have previously demonstrated IDC), or alternatively, in controlled nursery hydroponic conditions. When the assay is conducted in controlled nursery conditions, defined soils can be used, where the concentration of iron (e.g., available iron) has been previously measured. The plants can be scored at maturity, or at any time before maturity.

Fifteen (15) to twenty (20) soybean plants are planted and grown in a greenhouse. After a ten (10) day period, the plants are moved to a growth chamber. The growth chamber is kept at 25° C. day, 22° C. night with a relative humidity of 60% and light intensity of 200-500 microeinsteins and under a 16 hr photo-period. Water (3.5 gallons) plus the IDC nutrient solution is added to each test box. Water (3.5 gallons) plus the IDC nutrient solution and iron is added to the control box. Once boxes are filled with water and the solution, the pH is measured and adjusted to a range of 7.8-8.0. Nine (9) of the 15-20 plants are selected from each line. Two 3-plant groupings will be placed in two different boxes and the third grouping will be placed in the control box. Plants are kept in the growth chamber for a period of five (5) days. During that time, pH is measured and adjusted as necessary. At day five (5), all three (3) plants are evaluated as a group with a phenotypic score of 1-5. Plants receive a score of 1 if their leaves remain green, show no yellowing, and are comparable to the control within the control box. Additional scores will be given from a range of 1 (no yellowing) to 5 (severe yellowing) compared to their internal check lines. Nursey hydroponic conditions are normalized (1-9 scale) to correspond with disease ratings of soybean plants in field conditions.

The scoring system rates each plant on a scale of one (1) (most tolerant—no disease) to nine (9) (most susceptible—most severe disease), as shown in Table 11.

TABLE 11

IDC Score Ratings

| Plant or Plant Stand Score | Symptoms |
|---|---|
| 9 | Most plants are completely dead. The plants that are still alive are approximately 10% of normal height, and have very little living tissue. |
| 8 | Most leaves are almost dead, most stems are still green. Plants are severely stunted (10-20% of normal height). |
| 7 | Most plants are yellow and necrosis is seen on most leaves. Most plants are approximately 20-40% of normal height. |
| 6 | Most plants are yellow, and necrosis is seen on the edges of less than half the leaves. Most plants are approximately 50% of normal height. |
| 5 | Most plants are light green to yellow, and no necrosis is seen on the leaves. Most plants are stunted (50-75% of normal height). |
| 4 | More than half the plants show moderate chlorosis, but no necrosis is seen on the leaves. |
| 3 | Less than half of the plants showing moderate chlorosis (light green leaves). |
| 2 | A few plants are showing very light chlorosis on one or two leaves. |
| 1 | All plants are normal green color. |

It will be appreciated that any such scale is relative, and furthermore, there may be variability between practitioners as to how the individual plants and the entire stand as a whole are scored. Optionally, the degree of chlorosis can be measured using a chlorophyll meter, e.g., a Minolta SPAD-502 Chlorophyll Meter, where readings off a single plant or a stand of plants can be made. Optionally, multiple readings can be obtained and averaged.

In general, while there is a certain amount of subjectivity to assigning severity measurements for disease symptoms, assignment to a given scale as noted above is well within the ordinary skill of a practitioner in the field. Measurements can also be averaged across multiple scores to reduce variation in field measurements.

V. Introgression of a Genomic Region Associated with a Low Iron Growth Condition Tolerance Phenotype Provided herewith are unique soybean germplasms comprising one or more introgressed genomic regions, QTL, or polymorphic nucleic acid markers associated with a low iron growth condition tolerant phenotype and methods of obtaining the same. Marker-assisted introgression involves the transfer of a chromosomal region, defined by one or more markers, from one germplasm to a second germplasm. Offspring of a cross that contain the introgressed genomic region can be identified by the combination of markers characteristic of the desired introgressed genomic locus from a first germplasm (e.g., a low iron growth condition tolerant germplasm) and both linked and unlinked markers characteristic of the desired genetic background of a second germplasm (e.g., a low iron growth condition susceptible germplasm). In addition to the polymorphic nucleic acid markers provided herewith that identify alleles of certain QTL associated with a low iron growth condition tolerant phenotype, flanking markers that fall on both the telomere proximal end and the centromere proximal end of the genomic intervals comprising the QTL are also provided in Tables 1-10. Such flanking markers are useful in a variety of breeding efforts that include, but are not limited to, introgression of genomic regions associated with a low iron growth condition tolerant phenotype into a genetic background comprising markers associated with germplasm that ordinarily contains a genotype associated with a susceptible phenotype and maintenance of those genomic regions associated with a low iron growth condition tolerant phenotype in a plant population. Numerous markers that are linked and either immediately adjacent or adjacent to a low iron growth condition tolerant QTL in soybean that permit introgression of low iron growth condition tolerant QTL in the absence of extraneous linked DNA from the source germplasm containing the QTL are provided herewith. In certain embodiments, the linked and immediately adjacent markers are within about 105 kilobases (kB), 80 kB, 60 kB, 50 kB, 40 kB, 30 kB, 20 kB, 10 kB, 5 kB, 1 kB, 0.5 kB, 0.2 kB, or 0.1 kB of the introgressed genomic region. In certain embodiments, the linked and adjacent markers are within 1,000 kB, 600 kB, 500 kB, 400 kB, 300 kB, 200 kB, or 150 kB of the introgressed genomic region. In certain embodiments, the linked markers are genetically linked within about 50 cM, 40 cM, 30 cM, 20 cM, 10 cM, 5 cM, 4 cM, 3 cM, 2 cM, or 1 cM of the introgressed genomic region. In certain embodiments, genomic regions comprising some or all of one or more of a low iron growth condition tolerant QTL described herein can be introgressed into the genomes of susceptible varieties by using markers that include, but are not limited to, genetically linked markers, adjacent markers, and/or immediately adjacent markers provided in Tables 1-10. Those skilled in the art will appreciate that when seeking to introgress a smaller genomic region comprising a low iron growth condition tolerant QTL locus described herein, that any of the telomere proximal or centromere proximal markers that are genetically linked to or immediately adjacent to a larger genomic region comprising a low iron growth condition tolerant QTL locus can also be used to introgress that smaller genomic region.

Provided herein are methods of introgressing any of the genomic regions comprising a low iron growth condition tolerance QTL locus of Tables 1-10 into soybean germplasm that lacks such a locus. In certain embodiments, the soybean germplasm that lacks such a genomic region comprising a low iron growth condition tolerance QTL locus of Tables 1-10 is susceptible or has less than optimal levels of tolerance to low iron growth conditions. In certain embodiments, the methods of introgression provided herein can yield soybean plants comprising introgressed genomic regions comprising one or more low iron growth condition tolerance QTL loci of Tables 1-10, where the immediately adjacent genomic DNA and/or some or all of the adjacent genomic DNA between the introgressed genomic region and the telomere or centromere will comprise allelic forms of the markers of Tables 1-11 that are characteristic of the germplasm into which the genomic region is introgressed and distinct from the germplasm from which the genomic region is derived. In certain embodiments, the soybean germplasm into which the genomic region is introgressed is germplasm that lacks such a low iron growth condition tolerance locus. In certain embodiments, the soybean germplasm into which the genomic region is introgressed is germplasm that lacks such a low iron growth condition tolerance locus and is either susceptible to low iron growth conditions or has less than optimal tolerance to low iron growth conditions.

Also provided herein are soybean plants produced by the aforementioned methods of introgression. In certain embodiments, the soybean plants will comprise introgressed genomic regions comprising a low iron growth condition tolerance QTL locus of Tables 1-10, where the immediately adjacent genomic DNA and/or some or all of the adjacent genomic DNA between the introgressed genomic region and the telomere or centromere will comprise allelic forms of the markers of Tables 1-10 that are characteristic of the germplasm into which the genomic region is introgressed and distinct from the germplasm from which the genomic region is derived.

Soybean plants or germplasm comprising an introgressed genomic region that is associated with a low iron growth condition tolerant phenotype, wherein at least 10%, 25%, 50%, 75%, 90%, or 99% of the remaining genomic sequences carry markers characteristic of soybean plants or germplasm that are otherwise or ordinarily comprise a genomic region associated with susceptibility to low iron growth conditions, are thus provided. Furthermore soybean plants comprising an introgressed region where closely linked regions adjacent and/or immediately adjacent to the genomic regions, QTL, and markers provided herewith that comprise genomic sequences carrying markers characteristic of soybean plants or germplasm that are otherwise or ordinarily comprise a genomic region associated with the susceptibility to low iron growth conditions are also provided.

Also provided herein are methods of creating a population of soybean plants with enhanced tolerance to low iron growth conditions. In certain embodiments, the maintenance of a low iron growth condition tolerance QTL locus is achieved by providing a population of soybean plants, detecting the presence of of a genetic marker that is genetically linked to the QTL, selecting one or more soybean plants containing said marker from the first population of soybean plants, and producing a population of offspring from the at least one selected soybean plants. In certain embodiments, the tolerance QTL are selected from Tables 1-10. In certain embodiments, the markers are genetically linked to the QTL in Tables 1-10. In certain embodiments, the markers are genetically linked to the tolerance QTL within 20 cM, 15 cM, 10 cM, 5 cM, 4 cM, or 3 cM. In certain embodiments, the genetic markers are selected from SEQ ID NOs. 1-147.

VI. Soybean Donor Plants Comprising Genomic Region Associated with Low Iron Growth Condition Phenotypes Low iron growth condition tolerance QTL allele or alleles can be introduced from any plant that contains that allele (donor) to any recipient soybean plant. In one aspect, the recipient soybean plant can contain additional low iron growth condition tolerance loci. In another aspect, the recipient soybean plant can contain a transgene. In another aspect, while maintaining the introduced QTL, the genetic contribution of the plant providing the low iron growth condition tolerance QTL can be reduced by back-crossing or other suitable approaches. In one aspect, the nuclear genetic material derived from the donor material in the soybean plant can be less than or about 50%, less than or about 25%, less than or about 13%, less than or about 5%, 3%, 2% or 1%, but that genetic material contains the low iron growth condition tolerance locus or loci of interest.

Plants containing one or more of the low iron growth condition tolerance loci described herein can be donor plants. In certain embodiments, a donor plant can be a susceptible line. In certain embodiments, a donor plant can also be a recipient soybean plant. A non-limiting and exemplary list of soybean varieties that are believed to comprise genomic regions associated with a low iron growth condition tolerance phenotype include, but are not limited to AG00501, AG00901, AG0131, AG0202, AG0231, AG0331, AG0401, AG801, AG0808, AG1031, AG1102, AG1230, AG2131, DKB22-52, AG3039, and AG3830 (Branded names of ASGROW (designated "AG") and DEKALB soybean varieties from Monsanto CO., 800 N. Lindbergh Blvd., St. Louis, Mo., USA.)

In a preferred embodiment, the soybean plants that comprise a genomic region associated with a low iron growth condition tolerance phenotype that are identified by use of the markers provided in Tables 1-10 and/or methods provided herein are soybean pre-commercial lines evaluated in an association study using a linear model and which is adjusted for stratification by principle components in the R GenABEL package.

In certain embodiment, a donor soybean plant is AG801 and derivatives thereof, and is used as the resistant parent in a bi-parental mapping population to select for genomic regions associated with a low iron growth condition tolerance phenotype.

Also provided herewith are additional soybean plants that comprise a genomic region associated with a low iron growth condition tolerance phenotype that are identified by use of the markers provided in Tables 1-11 and/or methods provided herein. Any of the soybean plants identified above or other soybean plants that are otherwise identified using the markers or methods provided herein can be used in methods that include, but are not limited to, methods of obtaining soybean plants with an introgressed low iron growth condition tolerance locus, obtaining a soybean plant that exhibits a low iron growth condition tolerance phenotype, or obtaining a soybean plant comprising in its genome a genetic region associated with a low iron growth condition tolerance phenotype.

In certain embodiments, the soybean plants provided herein or used in the methods provided herein can comprise a transgene that confers tolerance to glyphosate. Transgenes that can confer tolerance to glyphosate include, but are not limited to, transgenes that encode glyphosate tolerant Class I EPSPS (5-enolpyruvylshikimate-3-phosphate synthases) enzymes or glyphosate tolerant Class II EPSPS (5-enolpyruvylshikimate-3-phosphate synthases) enzymes. Useful glyphosate tolerant EPSPS enzymes provided herein are disclosed in U.S. Pat. No. 6,803,501, RE39,247, U.S. Pat. Nos. 6,225,114, 5,188,642, and 4,971,908. In certain embodiments, the glyphosate tolerant soybean plants can comprise a transgene encoding a glyphosate oxidoreductase or other enzyme which degrades glyphosate. Glyphosate oxidoreductase enzymes had been described in U.S. Pat. No. 5,776,760 and U.S. Reissue Pat. RE38,825. In certain embodiments the soybean plant can comprise a transgene encoding a glyphosate N-acetyltransferase gene that confers tolerance to glyphosate. In certain embodiments, the soybean plant can comprise a glyphosate n-acetyltransferase encoding transgene such as those described in U.S. Pat. No. 7,666,644. In still other embodiments, soybean plants comprising combinations of transgenes that confer glyphosate tolerance are provided. Soybean plants comprising both a glyphosate resistant EPSPS and a glyphosate N-acetyltransferase are also provided herewith. In certain embodiments, it is contemplated that the soybean plants used herein can comprise one or more specific genomic insertion(s) of a glyphosate tolerant transgene including, but not limited to, as those found in: i) MON89788 soybean (deposited under ATCC accession number PTA-6708 and described in US Patent Application Publication Number 20100099859), ii) GTS 40-3-2 soybean (Padgette et al., Crop Sci. 35: 1451-1461, 1995), iii) event 3560.4.3.5 soybean (seed deposited under ATCC accession number PTA-8287 and described in U.S. Patent Publication 20090036308), or any combination of i (MON89788 soybean), ii (GTS 40-3-2 soybean), and iii (event 3560.4.3.5 soybean).

A low iron growth condition tolerance associated QTL of the present invention may also be introduced into a soybean line comprising one or more transgenes that confer tolerance to herbicides including, but not limited to, glufosinate, dicamba, chlorsulfuron, and the like, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels among others. These agronomic traits can be provided by the methods of plant biotechnology as transgenes in soybean.

In certain embodiments, it is contemplated that genotypic assays that provide for non-destructive identification of the plant or plants can be performed either in seed, the emergence stage, the "VC" stage (i.e. cotyledons unfolded), the V1 stage (appearance of first node and unifoliate leaves), the V2 stage (appearance of the first trifoliate leaf), and thereafter. In certain embodiments, non-destructive genotypic assays are performed in seed using apparati and associated methods as described in U.S. Pat. Nos. 6,959,617; 7,134,351; 7,454,989; 7,502,113; 7,591,101; 7,611,842; and 7,685,768, which are incorporated herein by reference in their entireties. In certain embodiments, non-destructive genotypic assays are performed in seed using apparati and associated methods as described in U.S. Patent Application Publications 20100086963, 20090215060, and 20090025288, which are incorporated herein by reference in their entireties. Published U.S. Patent Applications US 2006/0042527, US 2006/0046244, US 2006/0046264, US 2006/0048247, US 2006/0048248, US 2007/0204366, and US 2007/0207485, which are incorporated herein by reference in their entirety, also disclose apparatus and systems for the automated sampling of seeds as well as methods of sampling, testing and bulking seeds. Thus, in certain embodiments, any of the methods provided herein can comprise screening for markers in individual seeds of a population wherein only seed with at least one genotype of interest is advanced.

VII. Molecular Assisted Breeding Techniques

Genetic markers that can be used in the practice of the instant invention include, but are not limited to, are Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD), and others known to those skilled in the art. Marker discovery and development in crops provides the initial framework for applications to marker-assisted breeding activities (U.S. Patent Applications 2005/0204780, 2005/0216545, 2005/0218305, and 2006/00504538). The resulting "genetic map" is the representation of the relative position of characterized loci (DNA markers or any other locus for which alleles can be identified) along the chromosomes. The measure of distance on this map is relative to the frequency of crossover events between sister chromatids at meiosis.

As a set, polymorphic markers serve as a useful tool for fingerprinting plants to inform the degree of identity of lines or varieties (U.S. Pat. No. 6,207,367). These markers can form a basis for determining associations with phenotype and can be used to drive genetic gain. The implementation of marker-assisted selection is dependent on the ability to detect underlying genetic differences between individuals.

Certain genetic markers for use in the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

In another embodiment, markers that include. but are not limited, to single sequence repeat markers (SSR), AFLP markers, RFLP markers, RAPD markers, phenotypic markers, isozyme markers, single nucleotide polymorphisms (SNPs), insertions or deletions (Indels), single feature polymorphisms (SFPs, for example, as described in Borevitz et al. 2003 Gen. Res. 13:513-523), microarray transcription profiles, DNA-derived sequences, and RNA-derived sequences that are genetically linked to or correlated with low iron growth condition tolerance loci, regions flanking low iron growth condition tolerance loci, regions linked to low iron growth condition tolerance loci, and/or regions that are unlinked to low iron growth condition tolerance loci can be used in certain embodiments of the instant invention.

In one embodiment, nucleic acid-based analyses for determining the presence or absence of the genetic polymorphism (i.e. for genotyping) can be used for the selection of seeds in a breeding population. A wide variety of genetic markers for the analysis of genetic polymorphisms are available and known to those of skill in the art. The analysis may be used to select for genes, portions of genes, QTL, alleles, or genomic regions (Genotypes) that comprise or are linked to a genetic marker that is linked to or correlated with low iron growth condition tolerance loci, regions flanking low iron growth condition tolerance loci, regions linked to low iron growth condition tolerance loci, and/or regions that are unlinked to low iron growth condition tolerance loci can be used in certain embodiments of the instant invention.

Herein, nucleic acid analysis methods include, but are not limited to, PCR-based detection methods (for example, TaqMan assays), microarray methods, mass spectrometry-based methods and/or nucleic acid sequencing methods. In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form.

Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. However, the compositions and methods of the present invention can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005)). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5' 3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R.F. Service Science (2006) 311:1544-1546.

The markers to be used in the methods of the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTLs, particularly in the case of genotypes.

What is claimed is:

1. A method of creating a population of soybean plants with a low iron growth condition tolerant phenotype, comprising:
   a. genotyping a first population of soybean plants or seeds;
   b. detecting in said first population of soybean plants or seeds at least one polymorphic nucleic acid marker linked by less than or equal to 10 cM to an allele of a sequence selected from the group consisting of SEQ ID NOs:71 to 82, wherein said allele is associated with a low iron growth condition tolerant phenotype;
   c. selecting based upon said genotyping a soybean plant or seed containing said allele;
   d. crossing or selfing said selected soybean plant or a plant produced from said selected seed; and
   e. producing from said crossing or selfing a population comprising at least one progeny soybean plant comprising said allele and a low iron growth condition tolerant phenotype;
   wherein said allele of SEQ ID NO:71 comprises an adenosine at position 650,
   wherein said allele of SEQ ID NO:72 comprises an adenosine at position 201,
   wherein said allele of SEQ ID NO:73 comprises an tyrosine at position 201,
   wherein said allele of SEQ ID NO:74 comprises an guanine at position 201,
   wherein said allele of SEQ ID NO:75 comprises an guanine at position 201,
   wherein said allele of SEQ ID NO:76 comprises an guanine at position 201,
   wherein said allele of SEQ ID NO:77 comprises an tyrosine at position 201,
   wherein said allele of SEQ ID NO:78 comprises an guanine at position 201,
   wherein said allele of SEQ ID NO:79 comprises an tyrosine at position 201,
   wherein said allele of SEQ ID NO:80 comprises an tyrosine at position 201,
   wherein said allele of SEQ ID NO:81 comprises an guanine at position 201, and
   wherein said allele of SEQ ID NO:82 comprises an tyrosine at position 201.

2. The method of claim 1, wherein said polymorphic nucleic acid marker is genetically linked by less than or equal to 5 cM to said allele of a sequence selected from the group consisting of SEQ ID NOs:71 to 82.

3. The method of claim 1, wherein said polymorphic nucleic acid marker is genetically linked by less than or equal to 10 cM to said allele of a sequence selected from the group consisting of SEQ ID NOs:71 to 79.

4. The method of claim 1, wherein said polymorphic nucleic acid marker is flanked by SEQ ID NO:71 and SEQ ID NO:82.

5. The method of claim 1, wherein said polymorphic nucleic acid marker is genetically linked by less than or equal to 5 cM to said allele of a sequence selected from the group consisting of SEQ ID NOs:71 to 79.

6. The method of claim 1, wherein said polymorphic nucleic acid marker is from a chromosome region flanked by any two sequences selected from the group consisting of SEQ ID NOs: 71 to 82.

7. The method of claim 1, wherein said marker locus is of a marker type selected from the group consisting of Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD).

8. The method of claim 1, wherein said detecting an allele comprises a method selected form the group consisting of a PCR-based detection method, a microarray method, a mass spectrometry-based method, and a nucleic acid sequencing method.

9. The method of claim 1, wherein said detecting an allele comprises a single base extension (SBE) assay.

10. The method of claim 1, wherein said molecular marker is within 1 cM from said allele of a sequence selected from the group consisting of SEQ ID NOs: 71 to 82.

11. The method of claim 1, wherein said allele comprises SEQ ID NO: 78.

12. The method of claim 1, wherein said allele comprises SEQ ID NO: 79.

13. The method of claim 1, wherein said polymorphic nucleic acid marker is within 10 cM to said allele of SEQ ID NO: 78.

14. The method of claim 1, wherein said polymorphic nucleic acid marker is within 10 cM to said allele of SEQ ID NO: 79.

15. The method of claim 1, wherein said allele comprises SEQ ID NO: 77.

16. The method of claim 1, wherein said polymorphic nucleic acid marker is within 10 cM to said allele of SEQ ID NO: 77.

17. The method of claim 1, wherein said molecular marker is within 1 cM from said allele of a sequence selected from the group consisting of SEQ ID NOs: 71 to 79.

18. The method of claim 1, wherein said at least one polymorphic nucleic acid marker comprises a sequence selected from group consisting of SEQ ID NOs: 71 to 82.

19. The method of claim 1, wherein said first population of soybean plants or seeds comprises at least one soybean plant or a plant grown from said seeds comprising a low iron growth condition tolerant phenotype.

* * * * *